US010265495B2

(12) United States Patent
Voss et al.

(10) Patent No.: US 10,265,495 B2
(45) Date of Patent: Apr. 23, 2019

(54) PRESSURE ACTUATED VALVE SYSTEMS AND METHODS

(71) Applicant: ResQSystems, Inc., Roseville, MN (US)

(72) Inventors: Greg Voss, Apple Valley, MN (US);
Keith Lurie, Minneapolis, MN (US);
Anja Metzger, Stillwater, MN (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 529 days.

(21) Appl. No.: 14/197,996

(22) Filed: Mar. 5, 2014

(65) Prior Publication Data

US 2015/0144138 A1 May 28, 2015

Related U.S. Application Data

(60) Provisional application No. 61/907,902, filed on Nov. 22, 2013.

(51) Int. Cl.
*A61M 16/00* (2006.01)
*A61M 16/20* (2006.01)
*A61M 16/06* (2006.01)

(52) U.S. Cl.
CPC ........ *A61M 16/206* (2014.02); *A61M 16/208* (2013.01); *A61M 16/0009* (2014.02);
(Continued)

(58) Field of Classification Search
CPC .......... A61M 16/0009; A61M 16/0066; A61M 16/06; A61M 16/0683; A61M 16/206;
(Continued)

(56) References Cited

U.S. PATENT DOCUMENTS

| 1,848,232 A | 3/1932 | Swope et al. |
| 2,325,049 A | 7/1943 | Frye et al. |

(Continued)

FOREIGN PATENT DOCUMENTS

| AU | 1487792 B | 10/1992 |
| AU | 60539 B | 11/1994 |

(Continued)

OTHER PUBLICATIONS

US 5,584,866 A, 12/1996, Kroll et al. (withdrawn)
(Continued)

*Primary Examiner* — Bradley H Philips
(74) *Attorney, Agent, or Firm* — The Webb Law Firm

(57) ABSTRACT

Systems and methods are provided for decreasing intracranial pressure and enhancing circulation, as well as for increasing the respiratory rate and encouraging spontaneous respiration. According to such methods, a valve system is coupled with a person's airway. The valve system has an exhalation valve and an patient port that interfaces with the person's airway. The exhalation valve includes a diaphragm having a textured surface. The diaphragm is positioned across an exhalation valve seat and contacts a distal end of the exhalation valve seat, and is configured to prevent or impede respiratory gas flow to the person's lungs until an expiratory pressure equals or exceeds an opening pressure of the exhalation valve, at which time the diaphragm moves away from the distal end to create an open exhaust channel.

18 Claims, 20 Drawing Sheets

(52) U.S. Cl.
CPC ......... *A61M 16/0066* (2013.01); *A61M 16/06* (2013.01); *A61M 16/0683* (2013.01); *A61M 2016/003* (2013.01); *A61M 2016/0027* (2013.01); *A61M 2202/0208* (2013.01); *A61M 2205/0222* (2013.01); *A61M 2205/0238* (2013.01); *A61M 2205/15* (2013.01); *A61M 2205/3331* (2013.01); *A61M 2205/583* (2013.01)

(58) Field of Classification Search
CPC ........ A61M 16/208; A61M 2016/0027; A61M 2016/003; A61M 2202/0208; A61M 2205/0222; A61M 2205/0238; A61M 2205/15; A61M 2205/3331
See application file for complete search history.

(56) References Cited

U.S. PATENT DOCUMENTS

| | | |
|---|---|---|
| 2,774,346 A | 12/1956 | Halliburton |
| 2,854,982 A | 10/1958 | Pagano |
| 2,904,898 A | 9/1959 | Marsden |
| 3,009,266 A | 11/1961 | Brook |
| 3,049,811 A | 8/1962 | Ruben |
| 3,068,590 A | 12/1962 | Padellford |
| 3,077,884 A | 2/1963 | Batrow et al. |
| 3,191,596 A | 6/1965 | Bird et al. |
| 3,199,225 A | 8/1965 | Robertson et al. |
| 3,209,469 A | 10/1965 | James |
| 3,216,413 A | 11/1965 | Arecheta Mota |
| 3,274,705 A | 9/1966 | Breakspear |
| 3,276,147 A | 10/1966 | Padellford |
| 3,307,541 A | 3/1967 | Hewson |
| 3,357,426 A | 12/1967 | Cohen |
| 3,420,232 A | 1/1969 | Bickford |
| 3,459,216 A | 8/1969 | Bloom et al. |
| 3,467,092 A | 9/1969 | Bird et al. |
| 3,509,899 A | 5/1970 | Hewson |
| 3,515,163 A | 6/1970 | Freeman |
| 3,523,529 A | 8/1970 | Kissen |
| 3,552,390 A | 1/1971 | Muller |
| 3,562,924 A | 2/1971 | Baermann et al. |
| 3,562,925 A | 2/1971 | Baermann et al. |
| 3,568,333 A | 3/1971 | Clark |
| 3,662,751 A | 5/1972 | Barkalow et al. |
| 3,669,108 A | 6/1972 | Sundblom et al. |
| 3,734,100 A | 5/1973 | Walker et al. |
| 3,739,776 A | 6/1973 | Bird et al. |
| 3,794,043 A | 2/1974 | McGinnis |
| 3,815,606 A | 6/1974 | Mazal |
| 3,834,383 A | 9/1974 | Weigl et al. |
| 3,872,609 A | 3/1975 | Smrcka |
| 3,874,093 A | 4/1975 | Garbe |
| 3,875,626 A | 4/1975 | Tysk et al. |
| 3,933,171 A | 1/1976 | Hay |
| 3,949,388 A | 4/1976 | Fuller |
| 3,973,564 A | 8/1976 | Carden |
| 3,981,398 A | 9/1976 | Boshoff |
| 3,993,059 A | 11/1976 | Sjostrand |
| 4,037,595 A | 7/1977 | Elam |
| 4,041,943 A | 8/1977 | Miller |
| 4,054,134 A | 10/1977 | Kritzer |
| 4,077,400 A | 3/1978 | Harrigan |
| 4,077,404 A | 3/1978 | Elam |
| 4,095,590 A | 6/1978 | Harrigan |
| 4,166,458 A | 9/1979 | Harrigan |
| 4,193,406 A | 3/1980 | Jinotti |
| 4,198,963 A | 4/1980 | Barkalow et al. |
| 4,226,233 A | 10/1980 | Kritzer |
| 4,237,872 A | 12/1980 | Harrigan |
| 4,240,419 A | 12/1980 | Furlong et al. |
| 4,259,951 A | 4/1981 | Chernack et al. |
| 4,262,667 A | 4/1981 | Grant |
| 4,297,999 A | 11/1981 | Kitrell |
| 4,298,023 A | 11/1981 | McGinnis |
| 4,316,458 A | 2/1982 | Hammerton-Fraser |
| 4,320,754 A | 3/1982 | Watson et al. |
| 4,326,507 A | 4/1982 | Barkalow |
| 4,331,426 A | 5/1982 | Sweeney |
| 4,349,015 A | 9/1982 | Alferness |
| 4,360,345 A | 11/1982 | Hon |
| 4,397,306 A | 8/1983 | Weisfeldt et al. |
| 4,424,806 A | 1/1984 | Newman et al. |
| 4,446,864 A | 5/1984 | Watson et al. |
| 4,448,192 A | 5/1984 | Stawitcke et al. |
| 4,449,526 A | 5/1984 | Elam |
| 4,481,938 A | 11/1984 | Lindley |
| 4,501,582 A | 2/1985 | Schulz |
| 4,513,737 A | 4/1985 | Mabuchi |
| 4,519,388 A | 5/1985 | Schwanbom et al. |
| 4,520,811 A | 6/1985 | White et al. |
| 4,533,137 A | 8/1985 | Sonne |
| 4,543,951 A | 10/1985 | Phuc |
| 4,588,383 A | 5/1986 | Parker et al. |
| 4,598,706 A | 7/1986 | Darowski et al. |
| 4,601,465 A | 7/1986 | Roy |
| 4,602,653 A | 7/1986 | Ruiz-Vela et al. |
| 4,637,386 A | 1/1987 | Baum |
| 4,738,249 A | 4/1988 | Linman et al. |
| 4,750,493 A | 6/1988 | Brader |
| 4,774,941 A | 10/1988 | Cook |
| 4,797,104 A | 1/1989 | Laerdal et al. |
| 4,807,638 A | 2/1989 | Sramek |
| 4,809,683 A | 3/1989 | Hanson |
| 4,827,935 A | 5/1989 | Geddes et al. |
| 4,828,501 A | 5/1989 | Ingenito et al. |
| 4,863,385 A | 9/1989 | Pierce |
| 4,881,527 A | 11/1989 | Lerman |
| 4,898,166 A | 2/1990 | Rose et al. |
| 4,898,167 A | 2/1990 | Pierce et al. |
| 4,928,674 A | 5/1990 | Halperin et al. |
| 4,932,879 A | 6/1990 | Ingenito et al. |
| 4,971,042 A | 11/1990 | Lerman |
| 4,971,051 A | 11/1990 | Toffolon |
| 4,984,987 A | 1/1991 | Brault et al. |
| 5,014,698 A | 5/1991 | Cohen |
| 5,016,627 A | 5/1991 | Dahrendorf et al. |
| 5,029,580 A | 7/1991 | Radford et al. |
| 5,042,500 A | 8/1991 | Norlien et al. |
| 5,050,593 A | 9/1991 | Poon |
| 5,056,505 A | 10/1991 | Warwick et al. |
| 5,083,559 A | 1/1992 | Brault et al. |
| 5,109,840 A | 5/1992 | Daleiden |
| 5,119,825 A | 6/1992 | Huhn |
| 5,150,291 A | 9/1992 | Cummings et al. |
| 5,163,424 A | 11/1992 | Kohnke |
| 5,183,038 A | 2/1993 | Hoffman et al. |
| 5,184,620 A | 2/1993 | Cudahy et al. |
| 5,188,098 A | 2/1993 | Hoffman et al. |
| 5,193,529 A | 3/1993 | Labaere |
| 5,193,544 A | 3/1993 | Jaffe |
| 5,195,896 A | 3/1993 | Sweeney et al. |
| 5,217,006 A | 6/1993 | McCulloch |
| 5,231,086 A | 7/1993 | Sollevi |
| 5,235,970 A | 8/1993 | Augustine |
| 5,238,409 A | 8/1993 | Brault et al. |
| 5,239,988 A | 8/1993 | Swanson et al. |
| 5,263,476 A | 11/1993 | Henson |
| 5,265,595 A | 11/1993 | Rudolph |
| 5,282,463 A | 2/1994 | Hammersley |
| 5,295,481 A | 3/1994 | Geeham |
| 5,301,667 A | 4/1994 | McGrail et al. |
| 5,305,743 A | 4/1994 | Brain |
| 5,306,293 A | 4/1994 | Zacouto |
| 5,312,259 A | 5/1994 | Flynn |
| 5,313,938 A | 5/1994 | Garfield et al. |
| 5,316,907 A | 5/1994 | Lurie |
| 5,330,514 A | 7/1994 | Egelandsdal et al. |
| 5,335,654 A | 8/1994 | Rapoport |
| 5,353,788 A | 10/1994 | Miles |
| 5,355,879 A | 10/1994 | Brain |
| 5,359,998 A | 11/1994 | Lloyd |
| 5,366,231 A | 11/1994 | Hung |

(56) References Cited

U.S. PATENT DOCUMENTS

| | | |
|---|---|---|
| 5,377,671 A | 1/1995 | Biondi et al. |
| 5,383,786 A | 1/1995 | Kohnke |
| 5,388,575 A | 2/1995 | Taube |
| 5,392,774 A | 2/1995 | Sato |
| 5,395,399 A | 3/1995 | Rosenwald |
| 5,397,237 A | 3/1995 | Dhont et al. |
| 5,398,714 A | 3/1995 | Price |
| 5,413,110 A | 5/1995 | Cummings et al. |
| 5,423,685 A | 6/1995 | Adamson et al. |
| 5,423,772 A | 6/1995 | Lurie |
| 5,425,742 A | 6/1995 | Joy |
| 5,437,272 A | 8/1995 | Fuhrman |
| 5,452,715 A | 9/1995 | Boussignac |
| 5,454,779 A | 10/1995 | Lurie et al. |
| 5,458,562 A | 10/1995 | Cooper |
| 5,468,151 A | 11/1995 | Egelandsdal et al. |
| 5,474,533 A | 12/1995 | Ward et al. |
| 5,477,860 A | 12/1995 | Essen-Moller |
| 5,490,820 A | 2/1996 | Schock et al. |
| 5,492,115 A | 2/1996 | Abramov et al. |
| 5,492,116 A | 2/1996 | Scarberry et al. |
| 5,496,257 A | 3/1996 | Kelly |
| 5,507,282 A | 4/1996 | Younes |
| 5,517,986 A | 5/1996 | Starr et al. |
| 5,544,648 A | 8/1996 | Fischer, Jr. |
| 5,549,106 A | 8/1996 | Gruenke et al. |
| 5,549,581 A | 8/1996 | Lurie |
| 5,551,420 A | 9/1996 | Lurie et al. |
| 5,557,049 A | 9/1996 | Ratner |
| 5,580,255 A | 12/1996 | Flynn |
| 5,582,182 A | 12/1996 | Hillsman |
| 5,588,422 A | 12/1996 | Lurie |
| 5,593,306 A | 1/1997 | Kohnke |
| 5,606,968 A | 3/1997 | Mang |
| 5,614,490 A | 3/1997 | Przybelski |
| 5,617,844 A | 4/1997 | King |
| 5,618,665 A | 4/1997 | Lurie |
| 5,619,665 A | 4/1997 | Emma |
| 5,628,305 A | 5/1997 | Melker |
| 5,632,298 A | 5/1997 | Artinian |
| 5,643,231 A | 7/1997 | Lurie |
| 5,645,522 A | 7/1997 | Lurie et al. |
| 5,657,751 A | 8/1997 | Karr, Jr. |
| 5,678,535 A | 10/1997 | DiMarco |
| 5,685,298 A | 11/1997 | Idris |
| 5,692,498 A | 12/1997 | Lurie et al. |
| 5,697,364 A | 12/1997 | Chua et al. |
| 5,701,883 A | 12/1997 | Hete et al. |
| 5,701,889 A | 12/1997 | Danon |
| 5,704,346 A | 1/1998 | Inoue |
| 5,720,282 A | 2/1998 | Wright |
| 5,722,963 A | 3/1998 | Lurie |
| 5,730,122 A | 3/1998 | Lurie |
| 5,735,876 A | 4/1998 | Kroll et al. |
| 5,738,637 A | 4/1998 | Kelly et al. |
| 5,743,864 A | 4/1998 | Baldwin, II |
| 5,782,883 A | 7/1998 | Kroll et al. |
| 5,794,615 A | 8/1998 | Estes |
| 5,806,512 A | 9/1998 | Abramov et al. |
| 5,814,086 A | 9/1998 | Hirschberg et al. |
| 5,817,997 A * | 10/1998 | Wernig .................. H01H 13/14 200/16 R |
| 5,823,185 A | 10/1998 | Chang |
| 5,823,787 A | 10/1998 | Gonzalez et al. |
| 5,827,893 A | 10/1998 | Lurie |
| 5,832,920 A | 11/1998 | Field |
| 5,853,292 A | 12/1998 | Eggert et al. |
| 5,881,725 A | 3/1999 | Hoffman et al. |
| 5,885,084 A | 3/1999 | Pastrick et al. |
| 5,891,062 A | 4/1999 | Schock et al. |
| 5,896,857 A | 4/1999 | Hely et al. |
| 5,916,165 A | 6/1999 | Duchon et al. |
| 5,919,210 A | 7/1999 | Lurie |
| 5,927,273 A | 7/1999 | Federowicz et al. |
| 5,937,853 A | 8/1999 | Strom |
| 5,941,710 A | 8/1999 | Lampotang et al. |
| 5,975,081 A | 11/1999 | Hood et al. |
| 5,977,091 A | 11/1999 | Nieman et al. |
| 5,984,909 A | 11/1999 | Lurie |
| 5,988,166 A | 11/1999 | Hayek |
| 6,001,085 A | 12/1999 | Lurie |
| 6,010,470 A | 1/2000 | Albery et al. |
| 6,029,667 A | 2/2000 | Lurie |
| 6,042,532 A | 3/2000 | Freed et al. |
| 6,062,219 A | 5/2000 | Lurie et al. |
| 6,078,834 A | 6/2000 | Lurie |
| 6,086,582 A | 7/2000 | Altman et al. |
| 6,123,074 A | 9/2000 | Hete et al. |
| 6,131,571 A | 10/2000 | Lampotang et al. |
| 6,155,257 A | 12/2000 | Lurie et al. |
| 6,155,647 A | 12/2000 | Albecker, III |
| 6,165,105 A | 12/2000 | Boutellier et al. |
| 6,167,879 B1 | 1/2001 | Sievers et al. |
| 6,174,295 B1 | 1/2001 | Cantrell et al. |
| 6,176,237 B1 | 1/2001 | Wunderlich et al. |
| 6,193,519 B1 | 2/2001 | Eggert et al. |
| 6,209,540 B1 | 4/2001 | Sugiura et al. |
| 6,224,562 B1 | 5/2001 | Lurie et al. |
| 6,234,916 B1 | 5/2001 | Carusillo et al. |
| 6,234,985 B1 | 5/2001 | Lurie et al. |
| 6,277,107 B1 | 8/2001 | Lurie |
| 6,296,490 B1 | 10/2001 | Bowden |
| 6,312,399 B1 | 11/2001 | Lurie et al. |
| 6,334,441 B1 * | 1/2002 | Zowtiak .................. F16K 15/148 128/205.24 |
| 6,356,785 B1 | 3/2002 | Snyder et al. |
| 6,369,114 B1 | 4/2002 | Weil et al. |
| 6,374,827 B1 | 4/2002 | Bowden et al. |
| 6,390,996 B1 | 5/2002 | Halperin et al. |
| 6,425,393 B1 | 7/2002 | Lurie et al. |
| 6,439,228 B1 | 8/2002 | Hete et al. |
| 6,459,933 B1 | 10/2002 | Lurie et al. |
| 6,463,327 B1 | 10/2002 | Lurie et al. |
| 6,486,206 B1 | 11/2002 | Lurie |
| 6,526,970 B2 | 3/2003 | DeVries et al. |
| 6,526,973 B1 | 3/2003 | Lurie et al. |
| 6,536,432 B2 | 3/2003 | Truschel |
| 6,544,172 B2 | 4/2003 | Toeppen-Sprigg |
| 6,555,057 B1 | 4/2003 | Barbut et al. |
| 6,578,574 B1 | 6/2003 | Kohnke |
| 6,584,973 B1 | 7/2003 | Biondi et al. |
| 6,587,726 B2 | 7/2003 | Lurie et al. |
| 6,595,213 B2 | 7/2003 | Bennarsten |
| 6,604,523 B2 | 8/2003 | Lurie et al. |
| 6,622,274 B1 | 9/2003 | Lee et al. |
| 6,631,716 B1 | 10/2003 | Robinson et al. |
| 6,656,166 B2 | 12/2003 | Lurie |
| 6,662,032 B1 | 12/2003 | Gavish et al. |
| 6,676,613 B2 | 1/2004 | Cantrell et al. |
| 6,726,634 B2 | 4/2004 | Freeman |
| 6,729,334 B1 | 5/2004 | Baran |
| 6,758,217 B1 | 7/2004 | Younes |
| 6,776,156 B2 | 8/2004 | Lurie et al. |
| 6,780,017 B2 | 8/2004 | Pastrick et al. |
| 6,792,947 B1 | 9/2004 | Bowden |
| 6,863,656 B2 | 3/2005 | Lurie |
| 6,877,511 B2 | 4/2005 | DeVries et al. |
| 6,935,336 B2 | 8/2005 | Lurie et al. |
| 6,938,618 B2 | 9/2005 | Lurie et al. |
| 6,986,349 B2 | 1/2006 | Lurie |
| 6,988,499 B2 | 1/2006 | Holt et al. |
| 7,011,622 B2 | 3/2006 | Kuyava et al. |
| 7,032,596 B2 | 4/2006 | Thompson et al. |
| 7,044,128 B2 | 5/2006 | Lurie |
| 7,066,173 B2 | 6/2006 | Banner et al. |
| 7,082,945 B2 | 8/2006 | Lurie |
| 7,096,866 B2 | 8/2006 | Be'eri et al. |
| 7,174,891 B2 | 2/2007 | Lurie et al. |
| 7,185,649 B2 | 3/2007 | Lurie |
| 7,188,622 B2 * | 3/2007 | Martin .................. A62B 18/10 128/205.24 |
| 7,195,012 B2 | 3/2007 | Lurie |
| 7,195,013 B2 | 3/2007 | Lurie |
| 7,204,251 B2 | 4/2007 | Lurie |

(56) References Cited

U.S. PATENT DOCUMENTS

| | | |
|---|---|---|
| 7,210,480 B2 | 5/2007 | Lurie et al. |
| 7,220,235 B2 | 5/2007 | Geheb et al. |
| 7,226,427 B2 | 6/2007 | Steen |
| 7,275,542 B2 | 10/2007 | Lurie et al. |
| 7,311,668 B2 | 12/2007 | Lurie et al. |
| 7,469,700 B2 | 12/2008 | Baran |
| 7,487,773 B2 | 2/2009 | Li |
| 7,500,481 B2 | 3/2009 | Delache et al. |
| 7,594,508 B2 | 9/2009 | Doyle |
| 7,650,181 B2 | 1/2010 | Freeman et al. |
| 7,682,312 B2 | 3/2010 | Lurie |
| 7,766,011 B2 | 8/2010 | Lurie |
| 7,793,659 B2 | 9/2010 | Breen |
| 7,824,436 B2 | 11/2010 | Barbut et al. |
| 7,836,881 B2 | 11/2010 | Lurie et al. |
| 7,899,526 B2 | 3/2011 | Benditt et al. |
| 8,011,367 B2 | 9/2011 | Lurie et al. |
| 8,108,204 B2 | 1/2012 | Gabrilovich et al. |
| 8,151,790 B2 | 4/2012 | Lurie et al. |
| 8,210,176 B2 | 7/2012 | Metzger et al. |
| 8,287,474 B1 | 10/2012 | Koenig et al. |
| 8,388,682 B2 | 3/2013 | Hendricksen et al. |
| 8,408,204 B2 | 4/2013 | Lurie |
| 8,702,633 B2 | 4/2014 | Voss et al. |
| 8,755,902 B2 | 6/2014 | Lurie et al. |
| 8,939,922 B2 | 1/2015 | Strand et al. |
| 9,238,115 B2 | 1/2016 | Marshall et al. |
| 2001/0003984 A1 | 6/2001 | Bennarsten et al. |
| 2001/0029339 A1 | 10/2001 | Orr et al. |
| 2001/0047140 A1 | 11/2001 | Freeman |
| 2002/0007832 A1 | 1/2002 | Doherty |
| 2002/0069878 A1 | 6/2002 | Lurie et al. |
| 2002/0104544 A1 | 8/2002 | Ogushi et al. |
| 2002/0170562 A1 | 11/2002 | Lurie et al. |
| 2002/0179090 A1 | 12/2002 | Boussignac |
| 2003/0000526 A1 | 1/2003 | Gobel |
| 2003/0062040 A1 | 4/2003 | Lurie et al. |
| 2003/0192547 A1 | 10/2003 | Lurie et al. |
| 2004/0016428 A9 | 1/2004 | Lurie |
| 2004/0058305 A1 | 3/2004 | Lurie et al. |
| 2004/0200473 A1 | 10/2004 | Lurie et al. |
| 2004/0200474 A1 | 10/2004 | Lurie |
| 2004/0210281 A1 | 10/2004 | Dzeng et al. |
| 2004/0211415 A1 | 10/2004 | Lurie |
| 2004/0211416 A1 | 10/2004 | Lurie |
| 2004/0211417 A1 | 10/2004 | Lurie |
| 2004/0231664 A1 | 11/2004 | Lurie et al. |
| 2004/0267325 A1 | 12/2004 | Geheb et al. |
| 2005/0016534 A1 | 1/2005 | Ost |
| 2005/0075531 A1 | 4/2005 | Loeb et al. |
| 2005/0126567 A1 | 6/2005 | Lurie |
| 2005/0165334 A1 | 7/2005 | Lurie |
| 2005/0199237 A1 | 9/2005 | Lurie |
| 2005/0217677 A1 | 10/2005 | Lurie et al. |
| 2005/0267381 A1 | 12/2005 | Benditt |
| 2006/0089574 A1 | 4/2006 | Paradis |
| 2006/0129191 A1 | 6/2006 | Sullivan et al. |
| 2006/0270952 A1 | 11/2006 | Freeman et al. |
| 2007/0017523 A1 | 1/2007 | Be-Eri et al. |
| 2007/0021683 A1 | 1/2007 | Benditt et al. |
| 2007/0060785 A1 | 3/2007 | Freeman et al. |
| 2007/0083677 A1* | 4/2007 | Cecka ............ A61M 16/208 710/1 |
| 2007/0199566 A1 | 8/2007 | Be'eri |
| 2007/0221222 A1 | 9/2007 | Lurie |
| 2007/0277826 A1 | 12/2007 | Lurie |
| 2008/0039748 A1 | 2/2008 | Palmer et al. |
| 2008/0047555 A1 | 2/2008 | Lurie et al. |
| 2008/0092891 A1 | 4/2008 | Cewers |
| 2008/0097258 A1 | 4/2008 | Walker |
| 2008/0097385 A1 | 4/2008 | Vinten-Johansen et al. |
| 2008/0108905 A1 | 5/2008 | Lurie |
| 2008/0255482 A1 | 10/2008 | Lurie |
| 2008/0257344 A1 | 10/2008 | Lurie et al. |
| 2009/0020128 A1* | 1/2009 | Metzger ............ A61M 16/0825 128/207.16 |
| 2009/0062701 A1 | 3/2009 | Yannopoulos et al. |
| 2009/0076573 A1 | 3/2009 | Burnett et al. |
| 2009/0164000 A1 | 6/2009 | Shirley |
| 2009/0277447 A1 | 11/2009 | Voss et al. |
| 2009/0299156 A1 | 12/2009 | Simpson et al. |
| 2010/0000535 A1 | 1/2010 | Wickham et al. |
| 2010/0147302 A1 | 6/2010 | Selvarajan et al. |
| 2010/0174278 A1 | 7/2010 | Barbut et al. |
| 2010/0179442 A1 | 7/2010 | Lurie |
| 2010/0186745 A1* | 7/2010 | Mashak ............ A61M 16/00 128/204.26 |
| 2010/0247682 A1 | 9/2010 | Gladwin et al. |
| 2010/0319691 A1 | 12/2010 | Lurie et al. |
| 2011/0056491 A1 | 3/2011 | Rumph et al. |
| 2011/0098612 A1 | 4/2011 | Lurie |
| 2011/0160782 A1 | 6/2011 | Lurie et al. |
| 2011/0201979 A1 | 8/2011 | Voss et al. |
| 2011/0297147 A1 | 12/2011 | Lick et al. |
| 2012/0016279 A1 | 1/2012 | Banville et al. |
| 2012/0203147 A1 | 8/2012 | Lurie et al. |
| 2012/0302908 A1 | 11/2012 | Hemnes et al. |
| 2012/0330199 A1 | 12/2012 | Lurie et al. |
| 2012/0330200 A1 | 12/2012 | Voss et al. |
| 2013/0118498 A1* | 5/2013 | Robitaille ......... A61M 16/0075 128/205.16 |
| 2013/0172768 A1 | 7/2013 | Lehman |
| 2013/0231593 A1 | 9/2013 | Yannopoulos et al. |
| 2013/0269701 A1 | 10/2013 | Lurie |
| 2014/0005566 A1 | 1/2014 | Homuth et al. |
| 2014/0048061 A1 | 2/2014 | Yannopoulos et al. |
| 2016/0287834 A1 | 10/2016 | Bennett |

FOREIGN PATENT DOCUMENTS

| | | |
|---|---|---|
| AU | 687942 | 7/1998 |
| CA | 668771 A | 8/1963 |
| CA | 2077608 A1 | 3/1993 |
| CA | 2214887 C | 7/2008 |
| CN | 1183731 | 6/1998 |
| DE | 2453490 A1 | 5/1975 |
| DE | 4308493 A1 | 9/1994 |
| EP | 0029352 A1 | 5/1981 |
| EP | 0139363 A1 | 5/1985 |
| EP | 0245142 A1 | 11/1987 |
| EP | 0367285 A2 | 5/1990 |
| EP | 0411714 A1 | 2/1991 |
| EP | 0 509 773 | 10/1992 |
| EP | 0560440 A1 | 9/1993 |
| EP | 0623033 A1 | 11/1994 |
| GB | 1344862 | 1/1974 |
| GB | 1465127 A | 2/1977 |
| GB | 2117250 A | 10/1983 |
| GB | 2139099 A | 11/1984 |
| JP | 2005000675 A | 1/2005 |
| JP | 2006524543 A | 11/2006 |
| JP | 2007504859 A | 3/2007 |
| WO | 9005518 A1 | 5/1990 |
| WO | 9302439 A1 | 2/1993 |
| WO | 9321982 A1 | 11/1993 |
| WO | 9426229 A1 | 11/1994 |
| WO | 95/13108 A1 | 5/1995 |
| WO | 9528193 A1 | 10/1995 |
| WO | 96/28215 A1 | 9/1996 |
| WO | 9820938 A1 | 5/1998 |
| WO | 9947197 A1 | 9/1999 |
| WO | 99/63926 A1 | 12/1999 |
| WO | 0020061 A1 | 4/2000 |
| WO | 0102049 A2 | 1/2001 |
| WO | 01/70092 | 9/2001 |
| WO | 01/70332 | 9/2001 |
| WO | 02/092169 | 11/2002 |
| WO | 2004096109 A3 | 11/2004 |
| WO | 2006088373 A1 | 8/2006 |
| WO | 2008147229 A1 | 12/2008 |
| WO | 2010044034 A1 | 4/2010 |

(56) References Cited

FOREIGN PATENT DOCUMENTS

| | | |
|---|---|---|
| WO | 2013/064888 A1 | 5/2013 |
| WO | 2013/096495 | 6/2013 |
| WO | 2014/026193 | 2/2014 |

OTHER PUBLICATIONS http://www.answers.com/Q/What_volume_of_air_do_YOU_breathe_in_a_1_hour_period_in_m3.*

International Search Report and Written Opinion dated Jul. 9, 2014 for International Patent Application No. PCT/US2014/22725 filed Mar. 10, 2014, 24 pages.

Aufderheide, T., et al., "Hyperventilation-induced hypotension during cardiopulmonary resuscitation," Circulation, Apr. 27, 2004, 109(16):1960-5.

Aufderheide, T., et al., "Standard cardiopulmonary resuscitation versus active compression-decompression cardiopulmonary resuscitation with augmentation of negative intrathoracic pressure for out-of-hospital cardiac arrest: A randomized trial," Lancet, 2011, vol. 377, pp. 301-311.

Cohen, Todd J. et al., "Active Compression-Decompression Resuscitation: a Novel Method of Cardiopulmonary Resuscitation", Department of Medicine and the Cardiovascular Research Institute, UC San Francisco, American Heart Journal (1992)124(5):1145-1150.

Cohen, Todd J. et al., "Active Compression-Decompression: A New Method of Cardiopulmonary Resuscitation", JAMA (Jun. 3, 1992) 267(21): 2916-2923.

Lindner, Karl H. et al., "Effects of Active Compression-Decompression Resuscitation on Myocardial and Cerebral Blood Flow in Pigs," Department of Anesthesiology and Critical Care Medicine, University of Ulm, Germany, Circulation (Oct. 7, 1993) 88(3):1254-1263.

Lurie, Keith G., et al., "Regulated to Death: The Matter of Informed Consent for Human Experimentation in Emergency Resuscitation Research," Cardiac Arrhythmia Center at the University of Minnesota, PACE (Jul. 1995) 18:1443-1447.

Segal, N., et al., "Ischemic Postconditioning at the Initiation of Cardiopulmonary Resuscitation Facilitates Cardiac and Cerebral Recovery After Prolonged Untreated Ventricular Fibrillation," Resuscitation, Apr. 18, 2012, 7 pages.

Yannopoulos, D., et al., "Controlled pauses at the initiation of sodium nitroprusside-enhanced cardiopulmonary resuscitation facilitate neurological and cardiac recovery after 15 minutes of untreated ventricular fibrillation," Critical Care Medicine, 2012, vol. 40, No. 5, 8 pages.

Yannopoulos, D., et al., "Intrathoracic pressure regulation improves vital organ perfusion pressures in normovolemic and hypovolemic pigs", Resuscitation (2006), 2934, pp. 1-9.

Yannopoulos, D., et al., "Intrathoracic Pressure Regulator During Continuous-Chest-Compression Advanced Cardiac Resuscitation Improves Vital Organ Perfusion Pressures in a Porcine Model of Cardiac Arrest", Circulation, 2005, pp. 803-811.

Yannopoulos, D., et al., "Intrathoracic Pressure Regulation Improves 24-Hour Survival in a Porcine Model of Hypovolemic Shock." Anesthesia & Analgesia, ITPR and Survival in Hypovolemic Shock, vol. 104, No. 1, Jan. 2007, pp. 157-162.

Yannopoulos, D., et al., "Sodium nitroprusside enhanced cardiopulmonary resuscitation improves survival with good neurological function in a porcine model of prolonged cardiac arrest," Critical Care Medicine, 2011, vol. 39, No. 6, 6 pages.

Advanced Circulatory Systems, Inc. (Jan. 2014), Emerging Data: The Resuscitation Outcomes Consortium (ROC) PRIMED Study on the Efficacy of the ITD (#49-0864-000,06) [Brochure], Roseville, MN:Advanced Circulatory Systems, Inc. 2 pages.

Advanced Circulatory Systems, Inc. (Jan. 2013), Emerging Data: The Resuscitation Outcomes Consortium (ROC) PRIMED Study on the Efficacy of the ITD (#49-0864-000,05) [Brochure], Roseville, MN:Advanced Circulatory Systems, Inc. 2 pages.

Advanced Circulatory Systems, Inc. (Mar. 2012), Benefits of the ResQPOD Based Upon the ROC PRIMED Study (#49-0864-000,04) [Brochure], Roseville, MN:Advanced Circulatory Systems, Inc. 2 pages.

Advanced Circulatory Systems, Inc. (Jan. 2012), Benefits of the ResQPOD Based Upon the ROC PRIMED Study (#49-0864-000,03) [Brochure], Roseville, MN:Advanced Circulatory Systems, Inc. 2 pages.

Advanced Circulatory Systems, Inc. (Aug. 2011),Early Intervention is Life-Saving in Cardiac Arrest (#49-0864-000,01) [Brochure], Roseville, MN:Advanced Circulatory Systems, Inc. 2 pages.

Advanced Circulatory Systems, Inc. (Aug. 2011),Early Intervention is Life-Saving in Cardiac Arrest (#49-0864-000,02) [Brochure], Roseville, MN:Advanced Circulatory Systems, Inc. 2 pages.

Advanced Circulatory Systems, Inc. (2013), ResQPOD More than a Heartbeat (#49-0336-000,08) [Brochure], Roseville, MN:Advanced Circulatory Systems, Inc. 2 pages.

Advanced Circulatory Systems, Inc. (2011), ResQPOD ITD:Strengthening the Chain of Survival (#49-0336000,06) [Brochure], Roseville, MN:Advanced Circulatory Systems, Inc. 2 pages.

Advanced Circulatory Systems, Inc. (2010), ResQPOD Impedance Threshold Device:Strengthening the Chain of Survival (#49-0336000,05) [Brochure], Roseville, MN:Advanced Circulatory Systems, Inc. 2 pages.

Advanced Circulatory Systems, Inc. (2010), ResQPOD Impedance Threshold Device:Strengthening the Chain of Survival (#49-0336000,04) [Brochure], Roseville, MN:Advanced Circulatory Systems, Inc. 2 pages.

Advanced Circulatory Systems, Inc. (2010), ResQPOD Impedance Threshold Device 10.0:Strengthening the Chain of Survival (#49-0336000,03) [Brochure], Roseville, MN:Advanced Circulatory Systems, Inc. 2 pages.

Advanced Circulatory Systems, Inc. (2006). ResQPOD® Circulatory Enhancer: Strengthening the Chain of Survival (#49-0336-000, 02). [Brochure]. Roseville.MN: Advanced Circulatory Systems, Inc., 2 pages.

Advanced Circulatory Systems, Inc. (2006). ResQPOD® Circulatory Enhancer: Strengthening the Chain of Survival (#49-0336-000, 01) [Brochure]. Roseville, MN: Advanced Circulatory Systems, Inc.. 2 pages.

Advanced Circulatory Systems. Inc. (2011). ResQPOD® Perfusion on Demand: ResQPOD Impedance Threshold Device (#49-0324-001, 05) [Brochure]. Roseville, MN: Advanced Circulatory Systems, Inc., 2 pages.

Advanced Circulatory Systems, Inc. (2011). ResQPOD® Perfusion on Demand: ResQPOD Impedance Threshold Device (#49-0324-001, 04) [Brochure]. Roseville, MN: Advanced Circulatory Systems, Inc.. 2 pages.

Advanced Circulatory Systems, Inc. (2010). ResQPOD® Perfusion on Demand: ResQPOD Impedance Threshold Device (#49-0324-001, 03) [Brochure]. Roseville, MN: Advanced Circulatory Systems, Inc., 2 pages.

Advanced Circulatory Systems,Inc. (2009). ResQPOD® Perfusion on Demand: ResQPOD Impedance Threshold Device (#49-0324-001, 02) [Brochure]. Roseville, MN: Advanced Circulatory Systems, Inc., 2 pages.

Advanced Circulatory Systems,lnc. (2005). Introducing ResQPOD® (#49-0324-000, 01) [Brochure]. Roseville, MN: Advanced Circulatory Systems, Inc., 2 pages.

Ambu InternationalNS Directions for use of Ambu® CardioPump™ Sep. 1992, 8 pages.

Babbs, Charles F.MD. PhD., CPR Techniques that Combine Chest and Abdominal Compression and Decompression: Hemodynamic Insights from a Spreadsheet Model, Circulation,1999, pp. 2146-2152.

Christenson, J.M.. "Abdominal Compressions During CPR: Hemodynamic Effects of Altering Timing and Force", The Journal of Emergency Medicine, vol. 10, pp. 257-266, 1992.

Dupuis, Yvon G., Ventilators—Theory and Clinical Application, pp. 447-448, 481, 496; Jan. 1986, Mosby Company.

Geddes, L.A. et al., "Inspiration Produced by Bilateral Electromagnetic, Cervical Phrenic Nerve Stimulation in Man," IEEE Transactions on Biomedical Engineering 38(9): 1047-1048 (Oct. 1991).

(56) References Cited

OTHER PUBLICATIONS

Geddes, L.A. et al., "Optimum Stimulus Frequency for Contracting the Inspiratory Muscles with chest Surface Electrodes to Produce Artificial respiration," Annals of Biomedical Engineering 18:103-108 (1990).

Geddes, L.A. et al., "Electrically Produced Artificial Ventilation," Medical Instrumentation, vol. 22(5); 263-271, 1988.

Geddes, L.A., "Eiectroventilation—A Missed Opportunity?", Biomedical Instrumentation & Technology, Jul./Aug. 1998, pp. 401-414.

Glenn, William W.L. et al.,"Diaphragm Pacing by Electrical Stimulation of the Phrenic Nerve," Neurosurgery 17(6): 974-984 (1985).

Glenn, William W.L., et al., "Twenty Years of Experience in Phrenic Nerve Stimulation to Pace the Diaphragm," Pace 9: 780-784 (Nov./Dec. 1986, Part I).

Guidelines for Cardiopulmonary Resuscitation and Emergency Cardiac Care, JAMA, 1992.

Kotze, P.L. et al., "Diaphragm Pacing in the Treatment of Ventilatory Failure," San. Deel68:223-224 (Aug. 17, 1995).

Laghi, Franco et al., "Comparison of Magnetic and Electrical Phrenic Nerve Stimulation in assessment of Diaphragmantic Contractility," American Physiological society, pp. 1731-1742 (1996).

Lurie, K., et. Al., Comparison of a 10-Breaths-Per-Minute Versus a 2-Breaths -Per-Minute Strategy During Cardiopulmonary Resuscitation in a Porcine Model of Cardiac Arrest,: Respiratory Care, 2008, vol. 53, No. 7, pp. 862-870.

Michigan Instruments, Inc.Thumper 1007CC Continuous Compression Cardiopulmonary Resuscitation System, obtained online Jul. 15, 2006 at http://WwW.michiganinstruments.com/resus-thumper.htm, 2 pages.

Mushin W. W. et al., "Automatic Ventilation of the Lungs—The Lewis-Leigh Inflating Valve," Blackwell Scientific, Oxford, GB, p. 838.

Schultz, J., et al., "Sodium nitroprusside enhanced cardiopulmonary resuscitation (SNPeCPR) improves vitalorgan perfusion pressures and carotid blood flow in a porcine modelof cardiac arrest," Resuscitation, 2012, vol. 83, pp. 374-377.

Shapiro et al., "Neurosurgical Anesthesia and Intracranial Hypertension" Chapter 54, Anesthesia; 3rd Edition; Ed. Ron Miller 1990.

Zhao, et. Al., Inhibation of a Myocardial Injury by Ischemic Postconditioning During RePerfusion:Comparison with Ischemic Preconditioning, Am. J. Physiol Heart Circ 285: H579-H588 (2003).

Zoll Autopulse Non-Invasive Cardiac Support Pump, obtained online on 715106 at http://www.zoll.com/product.aspx?id=84,1 page.

\* cited by examiner

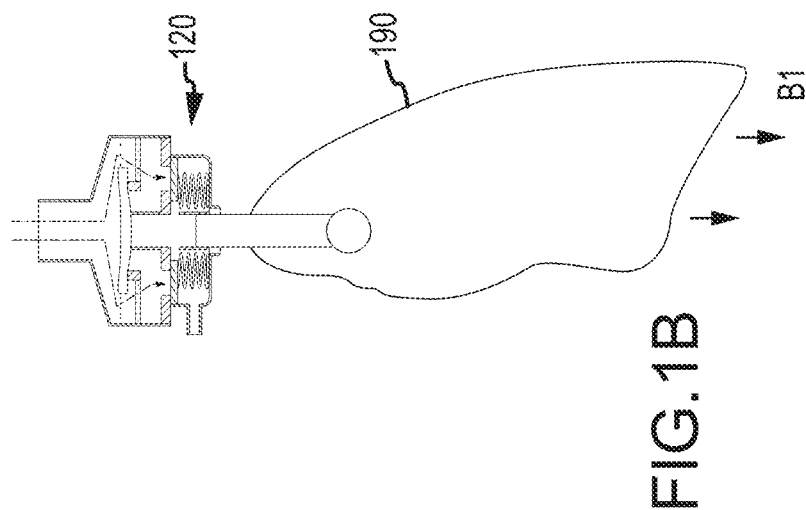
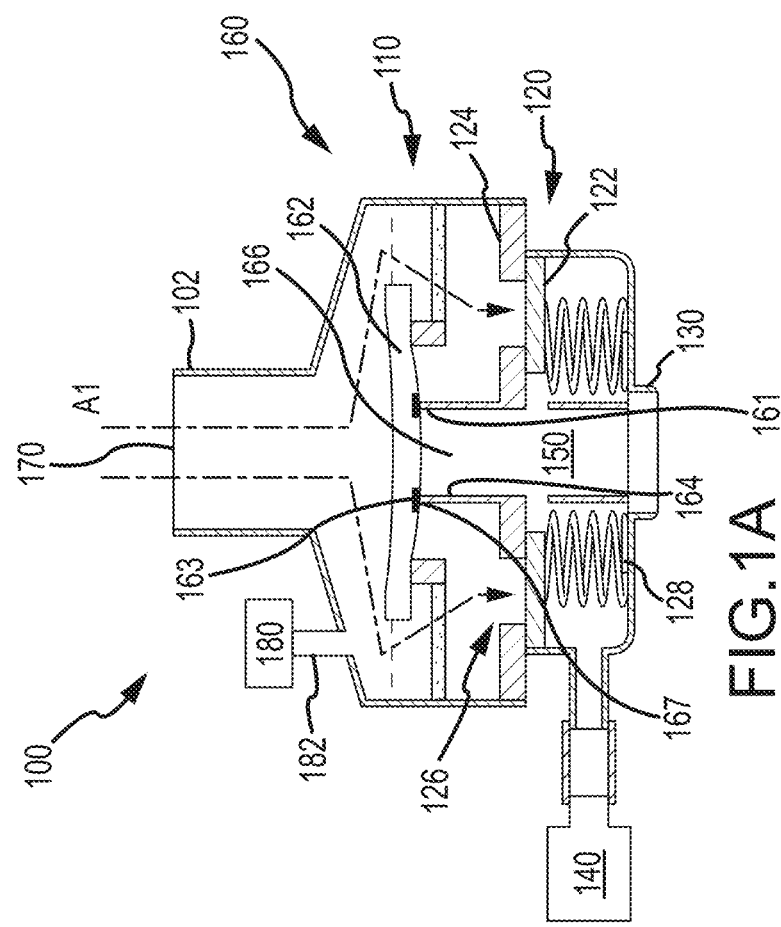

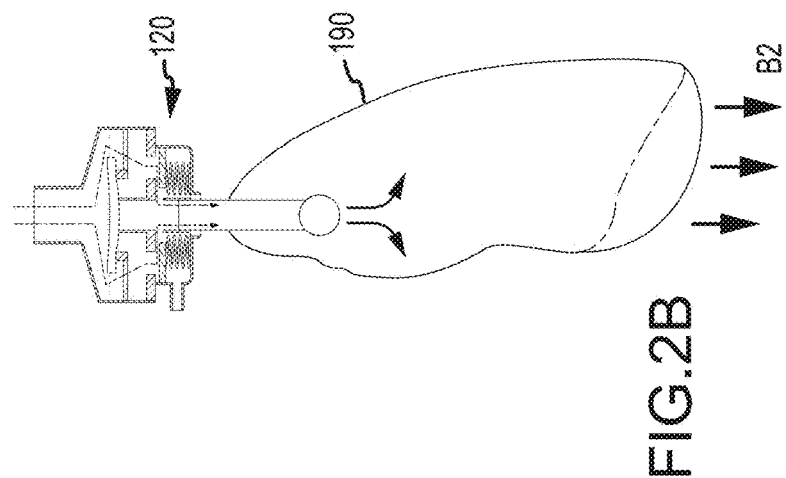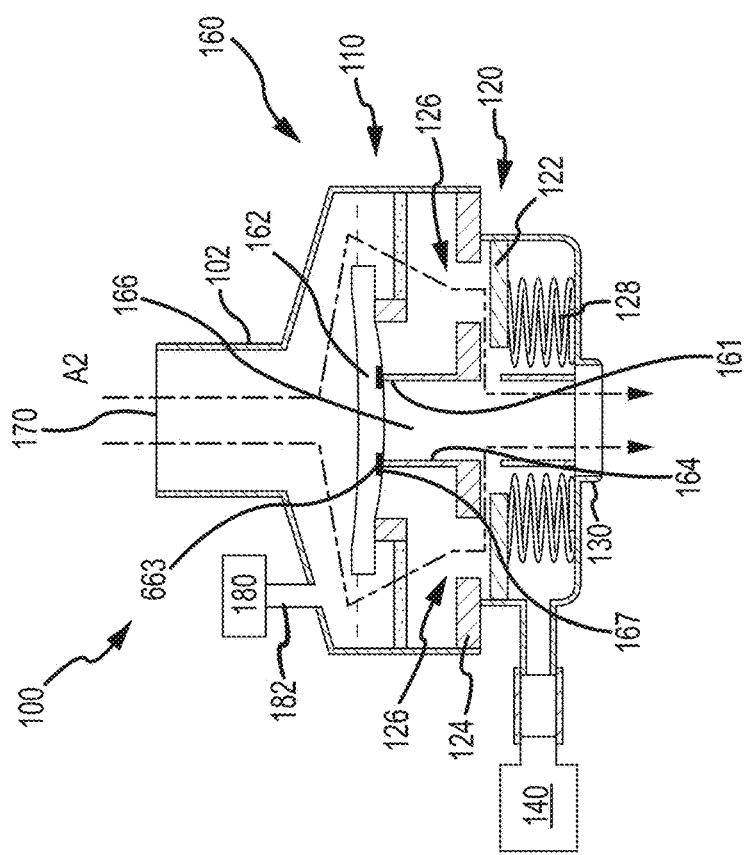

PRESSURE ACTUATED VALVE SYSTEMS AND METHODS

CROSS-REFERENCE TO RELATED APPLICATIONS

This application claims priority to U.S. Provisional Patent Application No. 61/907,902 filed Nov. 22, 2013, entitled "PRESSURE ACTUATED VALVE SYSTEMS AND METHODS," the entire disclosure of which is hereby incorporated by reference, for all purposes, as if fully set forth herein.

BACKGROUND OF THE INVENTION

Embodiments of the present invention relate generally to the field of circulatory enhancement, and in particular to systems and methods for increasing blood circulation, decreasing intracranial pressure, lowering end tidal carbon dioxide, and increasing the respiratory rate in a spontaneously breathing patient.

Millions of people suffer life-altering and life-threatening consequences from any of a variety of medical conditions and disease states that impair circulation. These medical conditions and disease states range from one-time occurrences to chronic conditions, and include shock, traumatic brain injury, cardiac arrest, dehydration, kidney failure, congestive heart failure, wound healing, diabetes, stroke, respiratory failure, and orthostatic hypotension. The consequences of reduced circulation are severe and burden the health care system with billions of dollars of expenditures on an annual basis.

Despite recent advances in the field of circulatory enhancement, the need for improved approaches for treating patients with impaired circulation remains an important medical challenge. For example, there is an ongoing need for non-invasive techniques that enhance circulation of blood throughout the body, thereby increasing the opportunity for survival and the quality of life of patients who experience major medical emergencies and severe circulatory conditions. Embodiments of the present invention provide effective solutions to at least some of these needs.

BRIEF SUMMARY OF THE INVENTION

Embodiments of the present invention provide systems and methods for increasing circulation of blood flow in individuals with states of low blood flow or perfusion, such as those suffering from sudden cardiac arrest, shock, and other hypotensive conditions. Persons that are in shock due to a variety of reasons including trauma, dehydration, cardiac arrest, or sepsis may suffer from dangerously low blood pressure. Persons subjected to head trauma or stroke may suffer from elevated intracranial pressures. Such persons can benefit from interventions which increase their blood circulation, decrease their intracranial pressure, and increase their cerebral perfusion pressure.

Circulation enhancement approaches disclosed herein are well suited for treating patients who are spontaneously breathing, such as, for example, those receiving dialysis. Additionally, the circulation enhancement techniques and equipment discussed herein are useful in treating non-breathing patients. For example, patients who experience cardiac arrest and are receiving cardio pulmonary resuscitation (CPR), in addition to those conditions mentioned above, can benefit from such circulatory enhancement techniques and equipment. Accordingly, such techniques and equipment can be beneficial in a plethora of clinical applications, including the treatment of cardiac arrest, intradialytic hypotension, dialysis, dehydration, diabetes, trauma and traumatic brain injury. Advantageously, these techniques can be used in any medical situation where an increase in circulation of blood is of benefit. Treatment embodiments can be administered by virtually anyone, from the layperson to the trained professional, and in any setting, including the home, a public venue, an ambulance, or a hospital. The medical systems and methods described herein can restore, maintain, or otherwise provide greater blood flow into the heart, resulting in increased cardiac output, which provides greater blood flow to the body's vital organs. Hence, these approaches can be used to restore life and improve the quality of life for patients suffering from cardiac arrest, low blood pressure, head injury, and the like.

Exemplary systems and methods provide non-invasive and instantaneous approaches for increasing the circulation of individuals in need thereof. In some instances, these techniques can use the body's biophysical performance to enhance circulation without the use of pharmaceutical or other mechanical agents. Often, treatment involves the use of a valve that selectively impedes inspiration during breathing, or during a decompression or relaxation phase of CPR. Inspiratory impedance can result in enhanced circulation, as evidenced by increased blood flow volume, cardiac output, and systolic blood pressure.

Techniques disclosed herein encompass systems and methods for providing safe, simple, and convenient treatment of low blood pressure in spontaneously breathing patients or non-breathing patients, typically those experiencing cardiac arrest. For example, such techniques can be used to increase blood pressure during hypotension from a variety of causes, including, without limitation, orthostatic intolerance, hypovolemia, heat shock, hemorrhagic shock, septic shock, dialysis, or blood donation. Embodiments of the present invention provide systems and methods for decreasing intracranial pressure and enhancing circulation in a breathing person, as well as for increasing the respiratory rate and encouraging spontaneous respiration. According to such embodiments, a valve system can be interfaced to a person's airway. The valve system can have a threshold valve and a patient port that interfaces with the patient's airway. The threshold valve can be configured to prevent or impede respiratory gas flow to the person's lungs during a portion of an inhalation event or other event resulting in a decrease in intrathoracic pressure, such as, for example, during the decompression or relaxation phase of CPR until an opening pressure of the threshold valve has been exceeded. By impeding or preventing respiratory gas flow to the patient's airway, the magnitude of the negative intrathoracic pressure is increased within the patient, thereby enhancing circulation. The incorporation of a non-stick coating on the threshold valve can ensure consistent actuation of the valve while reducing cracking pressure in the threshold valve.

Impedance threshold devices as described herein utilize the interdependence of the body's respiratory and circulatory systems to create a vacuum or negative pressure within the chest during the inspiratory phase of respiration. Embodiments of the present invention encompass systems and methods that are well suited for increasing or modulating negative intrathoracic pressure resulting in enhanced circulation in a patient. In some cases, an exemplary impedance threshold device (also referred to herein as an "ITD") provides an inspiration pressure waveform that has a square or substantially horizontal aspect. Such waveforms may be achieved with an ITD having a check valve gasket coated with a non-stick material, for example parylene type N. Advantageously, ITD's with coated check valve gaskets present improved operational properties during use, such as reliable and consistent cracking pressure characteristics. For example, an ITD having a check valve gasket coated with parylene at the seat area of the gasket valve which contacts the check valve housing can provide a reduced cracking pressure, in addition to a consistent and controllable negative pressure profiles in a patient during the inspiratory phase of respiration, as well as when performing CPR.

Patients experience hypotension for a variety of reasons, such as dialysis, blood donation or loss, orthostatic intolerance, dehydration, sepsis, excessive heat, drug overdose, spinal cord injury, and the like. Systems and method embodiments disclosed herein are well suited for increasing blood circulation in people who suffer from states of poor circulation and low blood flow that may be reflected in low blood pressure (hypotension). Advantageously, ITD's can be applied when a patient develops signs and symptoms associated with low blood pressure. Early signs of low central blood volume or hypoperfusion include tachypnea, tachycardia, delayed capillary refill, pallor and confusion. Late signs include hypotension, decreased cardiac output, cold temperature, cyanosis, combativeness, or unconsciousness.

Treatments that provide inspiratory resistance for increasing the circulation of blood flow in spontaneously breathing patients also often use a valve system to selectively reduce or minimize the resistance to expiration during breathing (or during the compression phase of CPR). Use of texture on a portion of a component of an exhalation valve can prevent leakage during inhalation or during decompression or recoil of the person's chest, while allowing for a lower opening pressure during exhalation or compression of the person's chest during CPR. The lower opening pressure ensures that the valve can open easily, with minimal or no expiratory resistance. This provides precise operation of the exhalation valve relative to atmospheric pressure during exhalation or the compression phase of CPR. Expiratory impedance can result in decreased circulation, as evidenced by decreased blood flow volume, cardiac output, and systolic blood pressure. The valve system can be interfaced to a person's airway. The valve system can include an exhalation valve and a patient port that can interface with the patient's airway. The exhalation valve can be configured to prevent or impede respiratory gas flow from the person's lungs during a portion of an exhalation event until the expiration equals or exceeds an opening pressure of the exhalation valve.

In some cases, an exemplary ITD provides an expiration pressure waveform that his substantially constant, or horizontal. For example, the expiration pressure waveform may be constant at approximately 0 cm $H_2O$. Such waveforms may be achieved with an ITD including a diaphragm having a textured surface. Advantageously, ITD's with textured diaphragms present unique operational properties during use, such as reliable and consistent cracking pressure characteristics. In some embodiments, the threshold valve and exhalation valve can be a single bi-directional valve. For example, a fishmouth valve could provide both inspiratory and expiratory functions.

Aspects of the invention provide a system for regulating intrathoracic pressure in a person. The system can include a valve system that is configured to be coupled with a person's airway. The valve system has an exhalation valve and a patient port that interfaces with the person's airway. The exhalation valve includes a diaphragm and an exhalation valve seat. The diaphragm has a textured surface that contacts a distal end of the exhalation valve seat. The exhalation valve can be configured to retain an intact seal between the textured surface of the diaphragm and the distal end of the exhalation valve seat during an inhalation phase (or decompression or recoil of the chest) and until an expiratory pressure of the person's airway during an exhalation phase (or compression of the lungs to expel air from the lungs) equals or exceeds an opening pressure of the exhalation valve. At such a time, the textured surface of the diaphragm separates from the distal end to create an open exhaust channel between the textured surface of the diaphragm and the distal end. The open exhaust channel can permit expiratory gas flow from the person's airway therethrough. The exhalation valve can also be used to impede or prevent respiratory gas flow from the patient's airway, which can create a positive end expiratory pressure within the patient to increase circulation. The incorporation of a textured surface on the diaphragm or the distal end of the exhalation valve seat can ensure consistent actuation of the valve while reducing leakage of the exhalation valve. The textured surface can be configured to provide a predictable opening pressure while limiting leakage of incoming respiratory gases through the exhalation valve during inspiration or a negative intrathoracic pressure to an acceptable leakage rate.

In one embodiment, the diaphragm and the exhalation valve seat separate from one another to create the open exhaust channel therebetween when pressure at the patient port exceeds pressure at the distal port by the operating threshold. In some embodiments, the exhalation valve includes a diaphragm and an exhalation valve seat. The operating threshold is influenced at least in part by a texturized interface between the diaphragm and the exhalation valve seat. The texturized interface can be defined by the exhalation valve seat and a texturized portion of the diaphragm. In some embodiments, the texturized portion of the diaphragm comprises one or more grooves. In other embodiments, the texturized portion of the diaphragm comprises one or more bumps. The texturized portion of the diaphragm can have a texture depth having a value within a range between 0.0005 and 0.001 inches. The texturized portion of the diaphragm can include a standard texture having a value of MT-11000. The operating threshold (opening pressure) of the exhalation valve can have a value within a range from 0 cm $H_2O$ to 8 cm $H_2O$. In some embodiments, the operating threshold (opening pressure) of the exhalation valve has a value between 0 cm $H_2O$ and 0.5 cm $H_2O$. The opening pressure of the exhalation valve can be relative atmospheric pressure or greater in some embodiments. In some embodiments, the acceptable leakage rate of the exhalation valve is below 0.05 lpm when the diaphragm contacts the distal end.

In some embodiments, the valve system can further include a patient port in fluid communication with the exhalation valve, and the patient port is configured to interface with the person's airway. The valve assembly can also include an inhalation valve that is configured to impede respiratory gas flow from the distal port to the patient port during an inhalation event or decompression or recoil of the chest when pressure at the distal port exceeds pressure at the patient port by an operating threshold of the inhalation valve. In some embodiments, the inhalation valve includes a check valve gasket that is coated with a coating. The coating can be configured to facilitate cracking of the threshold valve at the opening pressure of the threshold valve.

The threshold valve can be configured to produce a pressure that is represented by a square pressure waveform during an inspiration phase. In some embodiments, the threshold valve can provide a peak intrathoracic pressure of about −8 cm $H_2O$ or less during an inspiration phase. In other embodiments, the threshold valve can provide an intrathoracic pressure plateau of about −5 cm $H_2O$ or less during an inspiration phase. The coating may include a member selected from the group consisting of parylene type N, parylene type C, and parylene type D. In some embodiments, the coating is parylene type N.

In another aspect of the invention, a system for regulating intrathoracic pressure is provided. The system can include a patient port configured to permit respiratory gas flow, a distal port configured to permit respiratory gas flow, and a valve assembly disposed between, and in fluid communication with, the patient port and the distal port. The valve assembly includes an exhalation valve. The patient port can be positioned between the valve assembly and an airway of the person. The exhalation valve is configured to allow respiratory gas flow from the patient port to the distal port during an exhalation event or compression of the person's chest when pressure at the patient port exceeds the pressure at the distal port by an operating threshold of the exhalation valve. The operating threshold can include a range of pressure values extending between a minimum value and a maximum value such that a difference between the minimum value and the maximum value does not exceed about 0.5 cm $H_2O$.

In another aspect, the invention provides a pressure actuated valve for use in an intrathoracic pressure regulation system. The valve can include a conduit having a distal end that is substantially planar in geometry. The valve can further include a diaphragm that is positionable against the distal end to create an interface between at least a portion of the diaphragm and at least a portion of the distal end. The interface can include a textured surface on either the portion of the diaphragm or the portion of the distal end. The textured surface can be configured to provide a predictable opening pressure while limiting leakage of incoming respiratory gases through the exhalation valve during inspiration or a negative intrathoracic pressure to an acceptable leakage rate. The diaphragm can be configured to separate from the distal end, thus breaching the interface, to allow gases to flow between the diaphragm and the distal end when an expiratory pressure within the conduit is greater than between about 0 cm $H_2O$ and 0.5 cm $H_2O$. The pressure actuated valve can have an acceptable leakage rate below 0.05 lpm when the diaphragm is interfaced with the distal end. The textured surface can include one or more grooves or bumps. In some embodiments, the textured surface has a texture depth having a value within a range between about 0.0005 and 0.001 inches.

In one aspect, the invention provides a device for regulating intrathoracic pressure in a person. The device can include an atmospheric pressure sensor system that prevents all respiratory gas exchange when pressure inside of a patient's airway is less than atmospheric pressure. The sensor system includes a diaphragm, and the diaphragm includes a textured surface. The device can also include a sub-atmospheric pressure valve that opens at a predetermined sub-atmospheric pressure to allow respiratory gases to enter the patient's lungs. The device can additionally include a resistance regulator that controls expiratory resistance to allow for a range of resistance values between less than 1 cm of water at a flow rate of 20 L per minute to up to 8 cm of water at a flow rate of 20 L per minute. In some cases, such as for a patient being treated with CPR, the resistance regulator can allow for a range of resistance values between less than 1 cm of water at a flow rate of 20 L per minute to up to 5 cm of water at a flow rate of 20 L per minute. The atmospheric sensor system can detect changes in the patient's airway. The changes are usable to give a device user feedback related to a therapy that is delivered.

In one aspect, the invention provides a device for regulating intrathoracic pressure in a person. The device can include an atmospheric pressure sensor system having an exhalation valve that remains closed when pressure inside of a patient's airway is less than atmospheric pressure so as to impede flow from the patient. The sensor system includes a diaphragm and a valve seat. The diaphragm can include a textured surface. The device can also include a sub-atmospheric pressure valve that opens at a predetermined sub-atmospheric pressure at a patient port to allow respiratory gases to enter the patient's lungs.

In another aspect, the invention provides a device for regulating intrathoracic pressure in a person. The device can include a patient port configured to permit respiratory gas flow and a distal port configured to permit respiratory gas flow. The device can further include a valve assembly disposed between, and in fluid communication with, the patient port and the distal port. The valve assembly can include an atmospheric pressure sensor system having an exhalation valve that remains closed when pressure at the patient port is less than pressure at the distal port by so as to impede airflow from the patient. The exhalation valve opens when pressure at the patient port exceeds pressure at the distal port by an operating threshold of the exhalation valve. By monitoring an open or closed position of the exhalation valve, the atmospheric pressure sensor system indicates whether the pressure at the patient port is less than or greater than the pressure at the distal port. The sensor system includes a diaphragm and a valve seat. The diaphragm can include a textured surface. The device can further include a sub-atmospheric pressure valve that opens when pressure at the distal port exceeds pressure at the patient port by an operating threshold of the inhalation valve to allow respiratory gases to enter the patient's lungs. The operating threshold can include a range of pressure values extending between a minimum value and a maximum value such that a difference between the minimum value and the maximum value does not exceed about 0.5 cm $H_2O$.

In another aspect, the invention provides a method of regulating intrathoracic pressure in a person. The method can include interfacing a valve system to a person's airway. The valve system has an exhalation valve and a patient port that interfaces with the person's airway. The exhalation valve includes a diaphragm and an exhalation valve seat. The diaphragm has a textured surface that contacts a distal end of the exhalation valve seat. The exhalation valve is configured to prevent or impede respiratory gas flow from the person's airway until an expiratory pressure of the person's airway equals or exceeds an opening pressure of the exhalation valve, at which time the diaphragm separates from the distal end to create an open exhaust channel between the diaphragm and the distal end. The textured surface can be configured to provide a predictable opening pressure while limiting leakage of incoming respiratory gases through the exhalation valve during inspiration or a negative intrathoracic pressure to an acceptable leakage rate. The exhalation valve can be configured to provide a substantially constant expiratory intrathoracic pressure of about 0 cm $H_2O$ during an exhalation phase or compression of the person's chest. The valve system can have an acceptable leakage rate below 0.5 lpm when the diaphragm engages the distal surface. The impeded respiratory gas can include outflowing respiratory gas during a period of an exhalation event or compression of the person's chest (expiration). In some embodiments, the opening pressure can be relative atmospheric pressure or greater. The predictable opening pressure can include a range of pressure values extending between a minimum value and a maximum value such that a difference between the minimum value and the maximum value does not exceed about 0.5 cm $H_2O$. The method can further include performing cardiopulmonary resuscitation (CPR) on the person by repeatedly compressing the person's chest. In some embodiments, performing CPR further includes actively lifting the person's chest between compressions. In some embodiments, the person is breathing, and the exhalation valve prevents or impedes respiratory gas flow from the person's airway until the expiratory pressure of the person's airway equals or exceeds the opening pressure of the exhalation valve.

In another aspect, the present invention provides a medical device for use in treating a person. The medical device can include an exhalation valve that has a diaphragm having a textured surface. The exhalation valve is configured to prevent or impede respiratory gas flow from the person's lungs until the expiration equals or exceeds an opening pressure of the exhalation valve. The medical device can further include a patient port in fluid communication with the valve. The patient port is configured to interface with the person's airway. The medical device can further include a threshold valve having a coating coupled with a valve gasket. The threshold valve can be configured to prevent or impede respiratory gas flow to the person's lungs during a portion of an inhalation event or decompression or recoil of the person's chest until the an opening pressure of the threshold valve is exceeded.

In one aspect, the invention provides a bidirectional atmospheric pressure sensor. The bidirectional pressure sensor can include an exhalation valve comprising a diaphragm having a textured surface. The exhalation valve is configured to prevent or impede respiratory gas flow to a person's lungs when a pressure within the pressure sensor is less than relative atmospheric pressure. The exhalation valve is configured to create an open exhaust channel when the pressure is greater than relative atmospheric pressure.

In another aspect, the invention provides a bidirectional atmospheric pressure sensor. The bidirectional pressure sensor can include an exhalation valve that has a diaphragm having a textured surface. The exhalation valve is configured to prevent or impede respiratory gas flow to a person's lungs when a pressure within the pressure sensor is less than relative atmospheric pressure. The exhalation valve is further configured to create an open exhaust channel when the pressure is greater than relative atmospheric pressure. The sensor provides an indication that airway pressure in the patient is greater than relative atmospheric pressure by opening an exhaust channel between the diaphragm textured surface and an exhaust valve seat. The airway pressure indication can include visible movement of the diaphragm. A housing of the exhalation valve can permit visual inspection of the diaphragm. The indication can be provided by at least one of a thermal sensor, a humidity sensor, an accelerometer, and an airflow sensor.

In one aspect, the invention provides a system for regulating intrathoracic pressure in a person. The system can include a patient port configured to permit respiratory gas flow and a distal port configured to permit respiratory gas flow. The system can also include a valve assembly disposed between, and in fluid communication with, the patient port and the distal port, the valve assembly comprising an inhalation valve and an exhalation valve. The patient port is configured for positioning between the valve assembly and an airway of the person. The inhalation valve is configured to impede respiratory gas flow from the distal port to the patient port during an inhalation event when pressure at the distal port exceeds pressure at the patient port by a predetermined amount. The predetermined amount is associated with an operating threshold of the inhalation valve. The exhalation valve is configured to allow respiratory gas flow from the patient port to the distal port during an exhalation event or compression of the chest when pressure at the patient port exceeds pressure at the distal port by a predetermined amount. The predetermined amount is associated with an operating threshold of the exhalation valve.

In one aspect, the invention provides a method of regulating intrathoracic pressure in a person. The method includes interfacing a valve system to a person's airway. The valve system has a threshold valve and a patient port that interfaces with the person's airway. The threshold valve includes a coating coupled with a valve gasket and is configured to prevent or impede respiratory gas flow to the person's lungs during a portion of an inhalation event or decompression or recoil of the person's chest until the inspiration equals or exceeds an opening pressure of the threshold valve. In some embodiments, the threshold valve can be configured to provide a peak intrathoracic pressure of less than about −12 cm $H_2O$ and in some cases less than about −10 cm $H_2O$ during an inspiration phase. The threshold valve can be configured to provide a peak intrathoracic pressure of less than about −8 cm $H_2O$ during an inspiration phase. In some embodiments, the threshold valve is configured to provide an intrathoracic pressure plateau of less than −10 cm $H_2O$ during an inspiration phase. In some cases, the threshold valve is configured to provide an intrathoracic pressure plateau of about −5 cm $H_2O$ or −4 cm $H_2O$ during an inspiration phase.

The threshold valve can be configured to provide a square pressure waveform during an inspiration phase. The threshold valve can be configured to provide a ratio of peak intrathoracic pressure to intrathoracic pressure plateau of about 8:5. In some embodiments, the threshold valve can be configured to provide an average intrathoracic pressure during an inspiration phase. In some embodiments, the threshold valve can be configured to provide an intrathoracic pressure during an inspiration phase. The threshold valve coating can include a member selected from the group consisting of parylene type N, parylene type C, and parylene type D. In some embodiments, the coating includes parylene type N.

In another aspect, the invention provides a system for regulating intrathoracic pressure in a breathing person. The system can include a valve system that is configured to be coupled with a person's airway. The valve system includes a threshold valve and a patient port that interfaces with the person's airway. The threshold valve includes a coating coupled with a valve gasket and is configured to prevent or impede respiratory gas flow to the person's lungs during a portion of an inhalation event or during decompression or recoil of the person's chest until an opening pressure of the threshold valve is exceeded.

In another aspect, the invention provides a medical device that includes a threshold valve having a coating coupled with a valve gasket. The threshold valve is configured to prevent or impede respiratory gas flow to the person's lungs during a portion of an inhalation event or during decompression or relaxation of the person's lungs until an opening pressure of the threshold valve is exceeded. The medical device can further include a patient port in fluid communication with the valve. The patient port is configured to interface with the person's airway.

In one aspect, the invention provides a medical device for use in the treatment of a person. The medical device can include a threshold valve configured to prevent or impede respiratory gas flow to the person's lungs during a portion of an inhalation event or during decompression or relaxation of the person's lungs until an opening pressure of the threshold valve is exceeded. The medical device can further include a patient port in fluid communication with the valve. The patient port is configured to interface with the person's airway. The threshold valve provides an inspiration pressure waveform that has a square aspect. The inspiration pressure waveform includes a range of pressure values extending between a minimum value and a maximum value such that a difference between the minimum value and the maximum value does not exceed about 12 cm $H_2O$. In cases, the difference between the minimum value and the maximum value does not exceed about 10 cm $H_2O$, and in other cases less than about 8 cm $H_2O$.

In another aspect, the invention provides a method for sensing an airway pressure within a person. The method can include monitoring an indication of an exhalation valve to determine whether the airway pressure at a patient port of a valve system is greater than a pressure at a distal port of the valve system of a diaphragm of an exhalation valve. The diaphragm has a textured surface. The exhalation valve is configured to prevent or impede respiratory gas flow to the person's lungs when the airway pressure at the patient port is less than the pressure at the distal port. The exhalation valve is configured to create an open exhaust channel when the airway pressure at the patient port is greater than the pressure at the distal port. The airway pressure indication can include visible movement of the diaphragm. A housing of the exhalation valve can permit assessment of the diaphragm. The indication can be provided by at least one of a thermal sensor, a humidity sensor, an accelerometer, and an airflow sensor.

In one aspect, embodiments of the present invention encompass systems for regulating intrathoracic pressure in a person. The systems can include a valve system that is configured to be coupled with a person's airway. The valve system may have an exhalation valve and a patient port that interfaces with the person's airway. The exhalation valve can include a diaphragm having a textured surface. The diaphragm is positioned across an exhalation valve seat and contacts a distal end of the exhalation valve seat and is configured to prevent or impede respiratory gas flow to the person's lungs until an expiratory pressure equals or exceeds an opening pressure of the exhalation valve, at which time the diaphragm moves away from the distal end to create an open exhaust channel. In some embodiments, the expiratory pressure equals 0 atmospheres of pressure. In some aspects, the impedance of respiratory gas flow is during a portion of an exhalation event or compression of the person's chest. In one embodiment, the texturized surface includes one or more grooves. In another embodiment, the texturized surface comprises one or more bumps. In aspects of the invention, the texturized surface can have a texture depth of between 0.0005 and 0.0025 inches. Preferably, the texture depth is between 0.0005 and 0.001 inches. Embodiments of the invention can have the opening pressure be less than about 0.5 cm $H_2O$. In another embodiment, the textured surface comprises a mold tech (MT) MT-11000 to MT-11020 standard texture. Preferably, the textured surface comprises a MT-11000 surface. The system can further include a threshold valve and a second patient port that interfaces with the person's airway. The threshold valve can have a coating coupled with a valve gasket and can be configured to prevent or impede respiratory gas flow to the person's lungs during a portion of an inhalation event or during decompression or recoil of the person's chest until an opening pressure of the threshold valve is exceeded.

For a fuller understanding of the nature and advantages of the present invention, reference should be had to the ensuing detailed description taken in conjunction with the accompanying drawings.

BRIEF DESCRIPTION OF THE DRAWINGS 1A and 1B illustrate aspects of a circulatory enhancement system according to embodiments of the present invention.

FIGS. 2A and 2B illustrate aspects of a circulatory enhancement system according to embodiments of the present invention.

Figure 4:
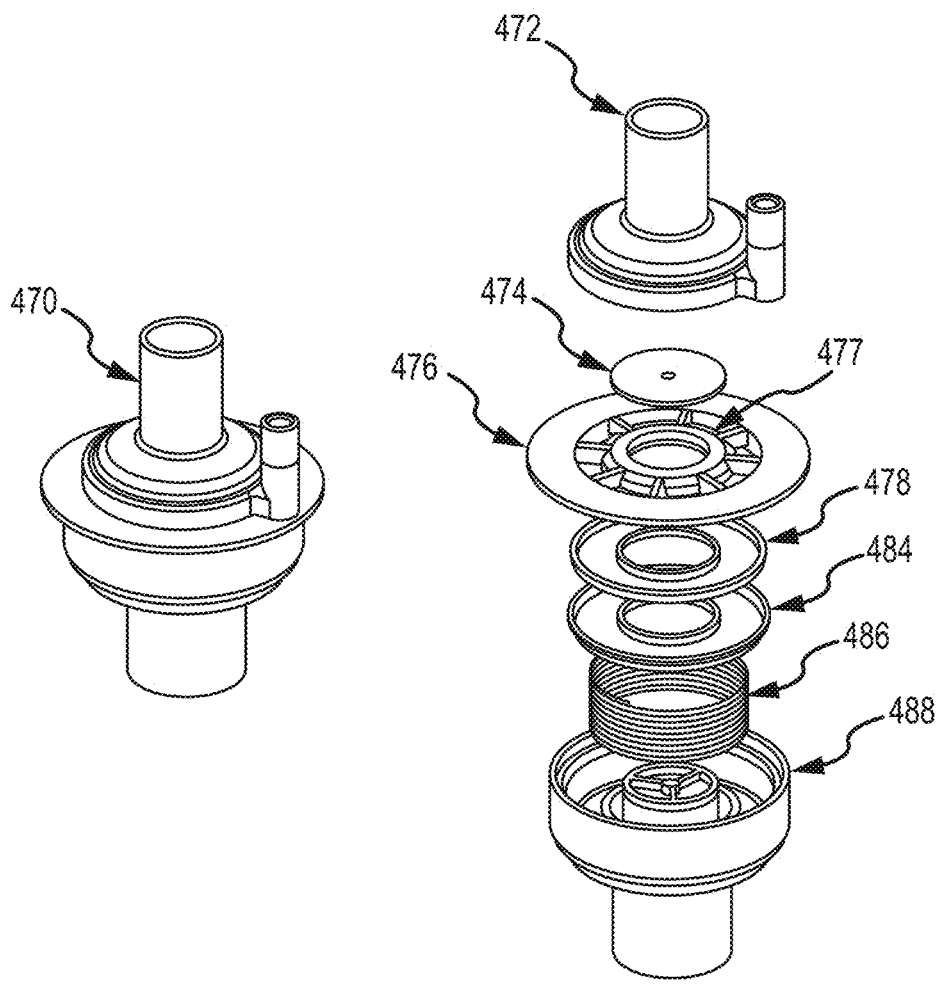
FIG. 4 illustrates an exploded view of a circulatory enhancement system according to embodiments of the present invention.
Figure 4A:
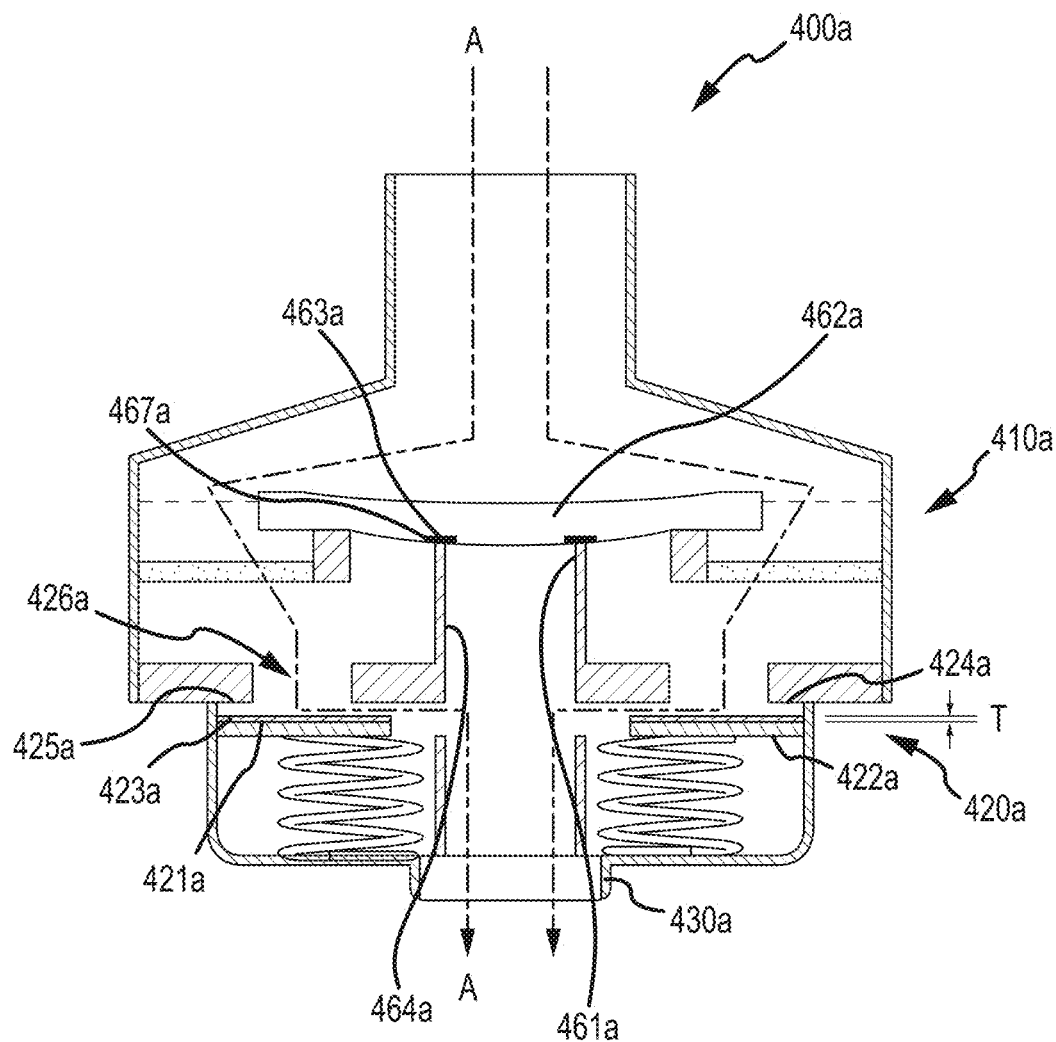
Figure 4B:
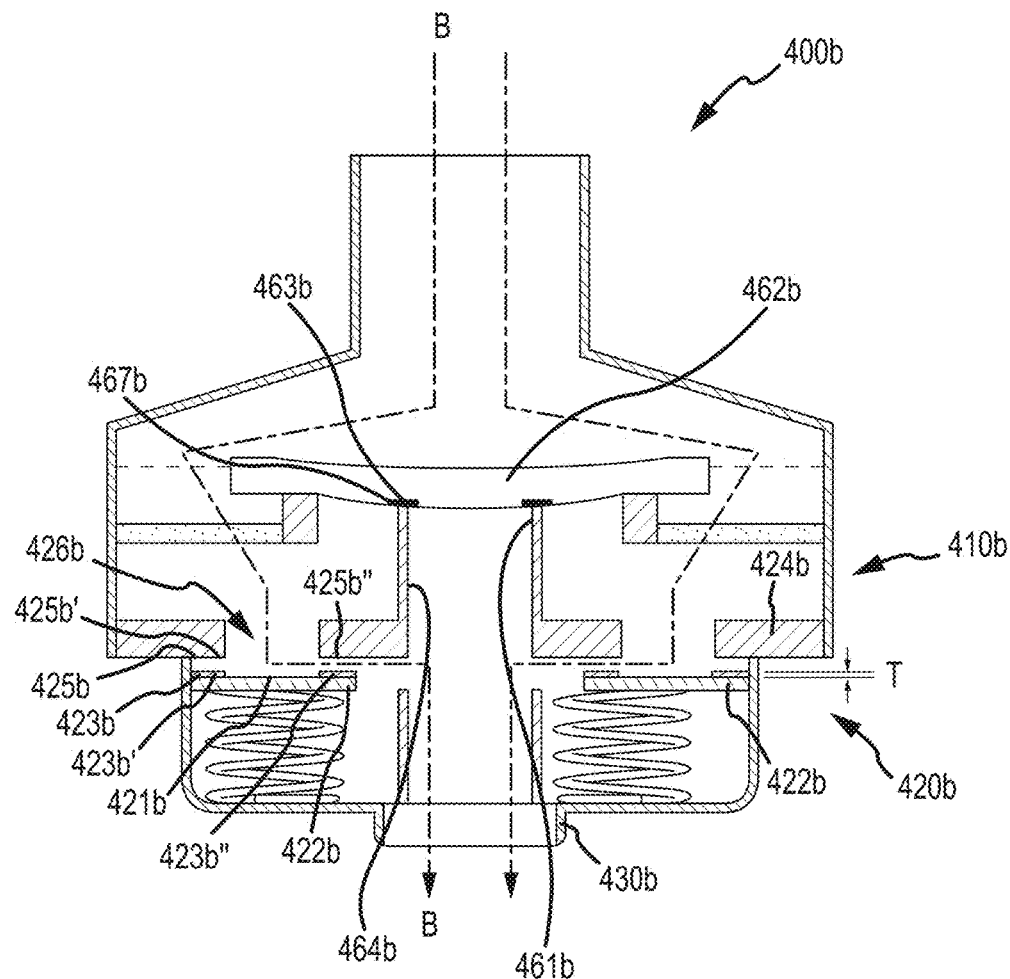
Figure 4C:
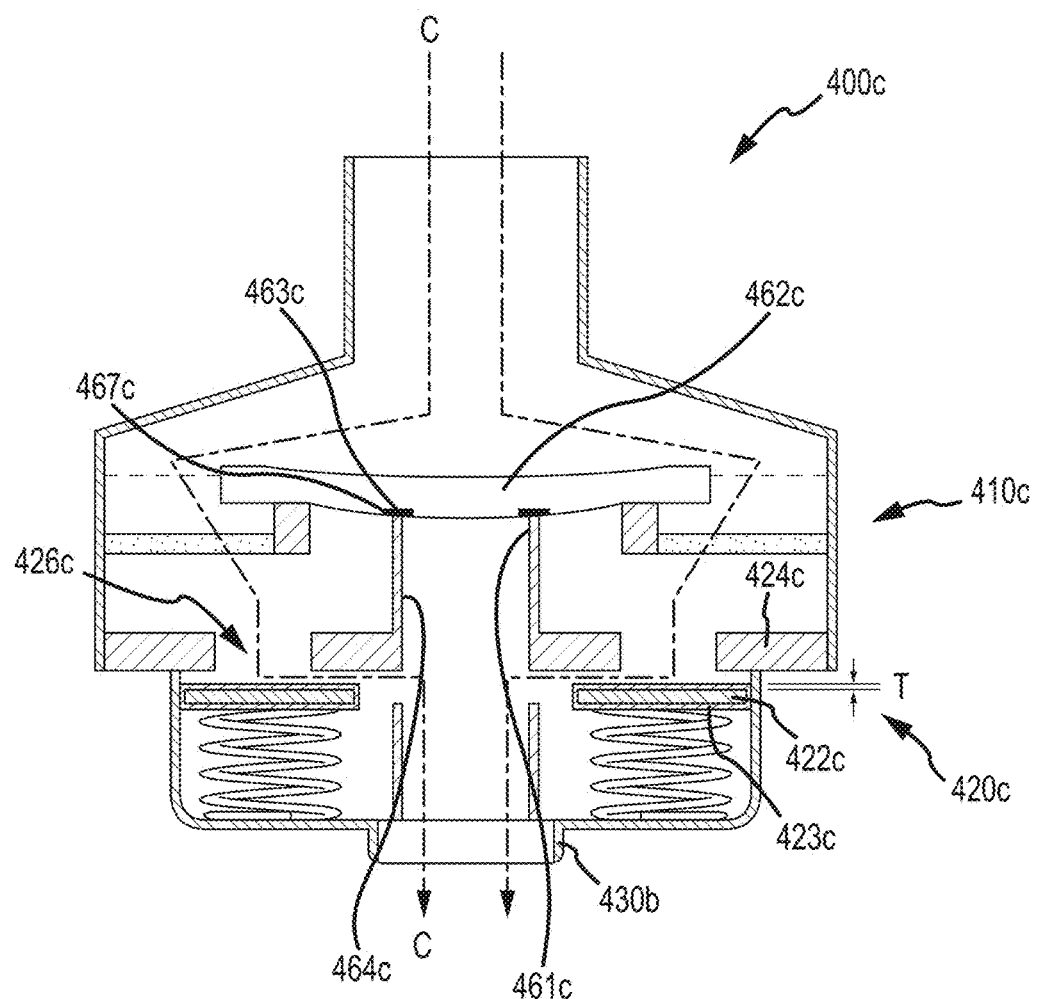

FIGS. 4A, 4B, and 4C illustrate aspects of a circulatory enhancement system according to embodiments of the present invention.

Figure 5A:
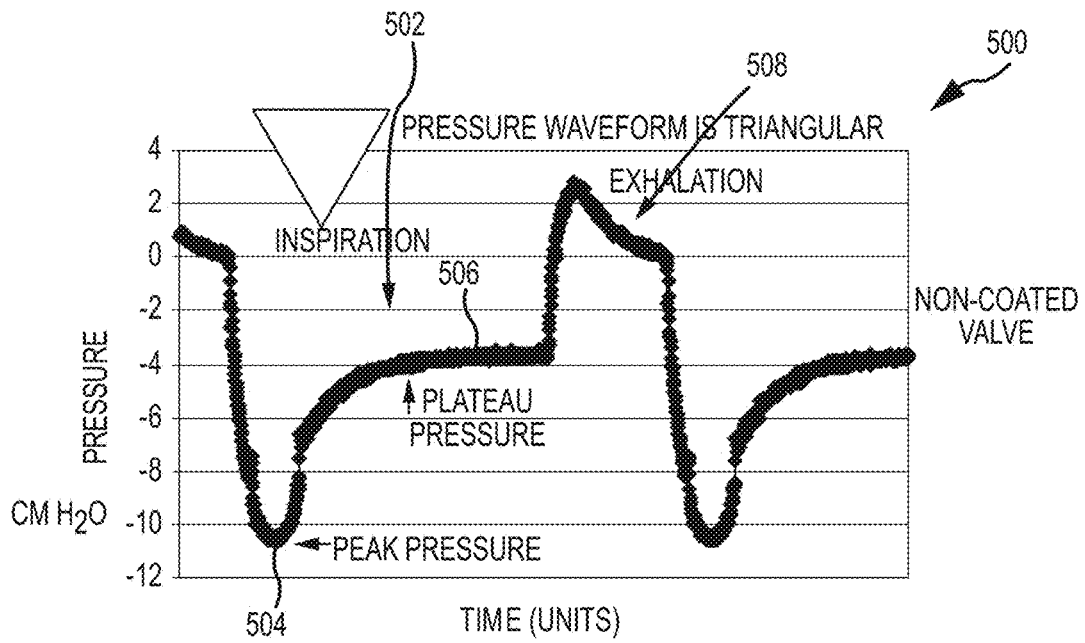
Figure 5B:
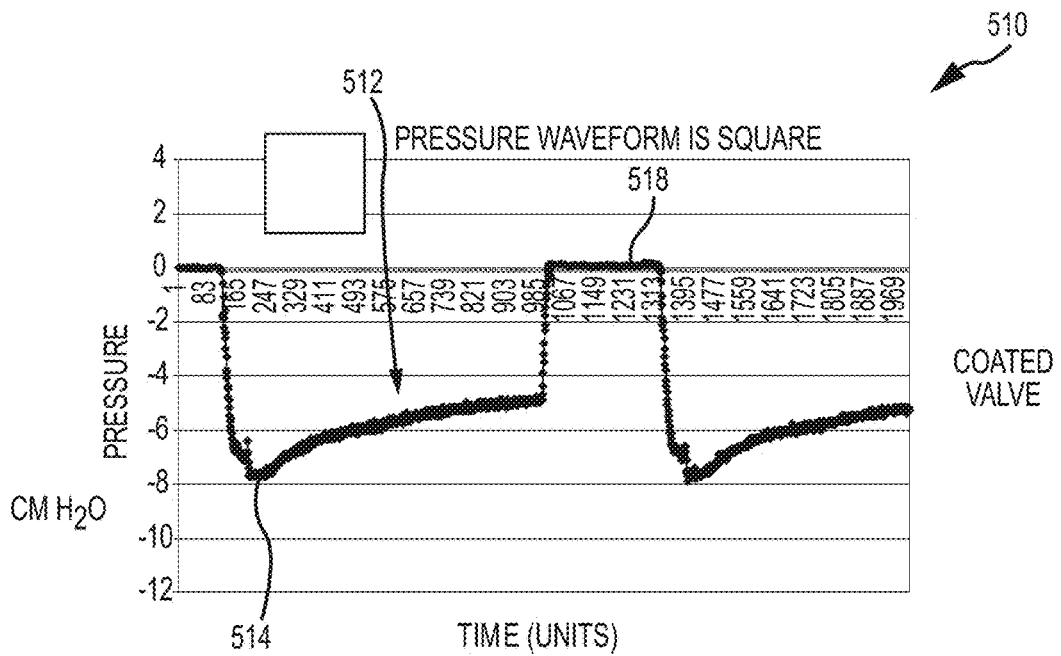

FIGS. 5A and 5B illustrate graphs showing a subject's intrathoracic pressure (ITP) over various spontaneous breathing cycles according to embodiments of the present invention.

Figure 6A:
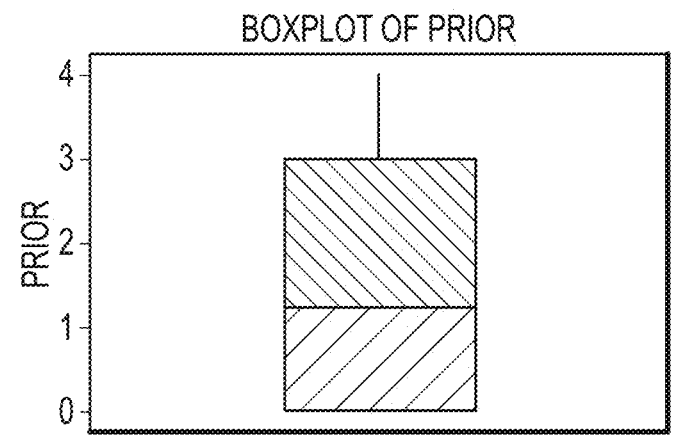
Figure 6B:
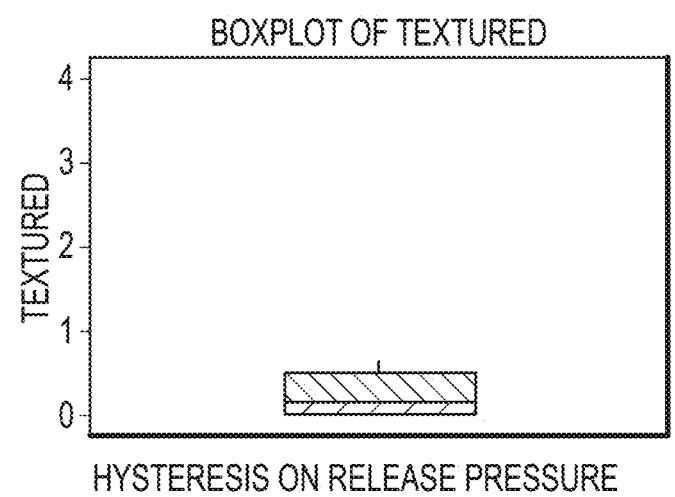
Figure 7:
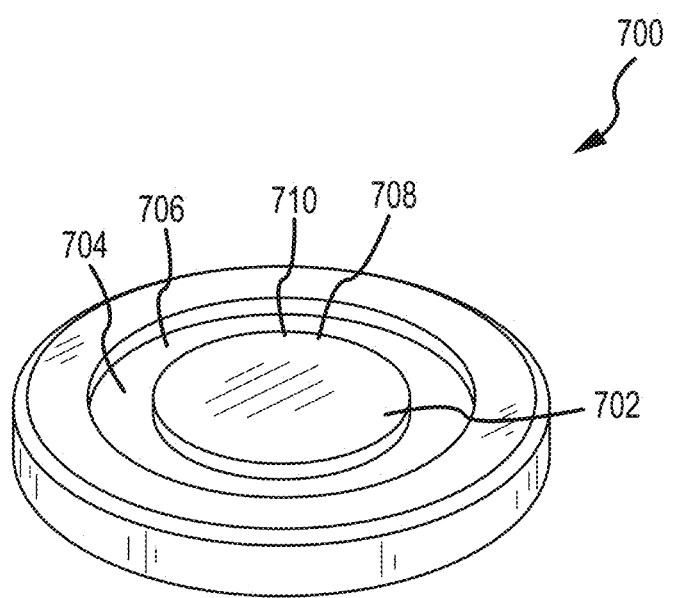
Figure 8:
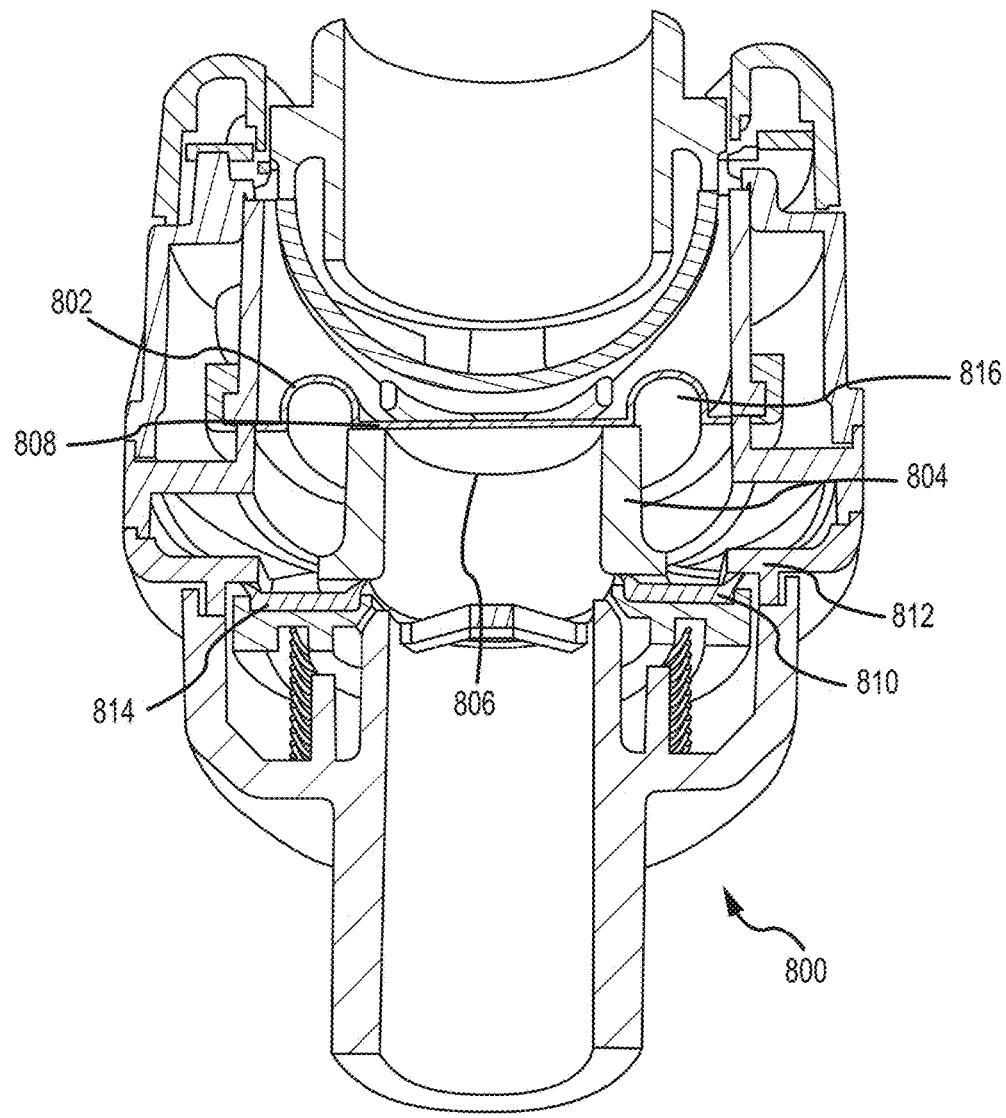

FIGS. 6A and 6B illustrate box plots of hysteresis on opening pressure for a circulatory enhancement system according to embodiments of the present invention FIG. 7 illustrates one aspect of a textured diaphragm according to embodiments of the present invention FIG. 8 shows a cross-section of one embodiment of a control valve system.

Figure 9:
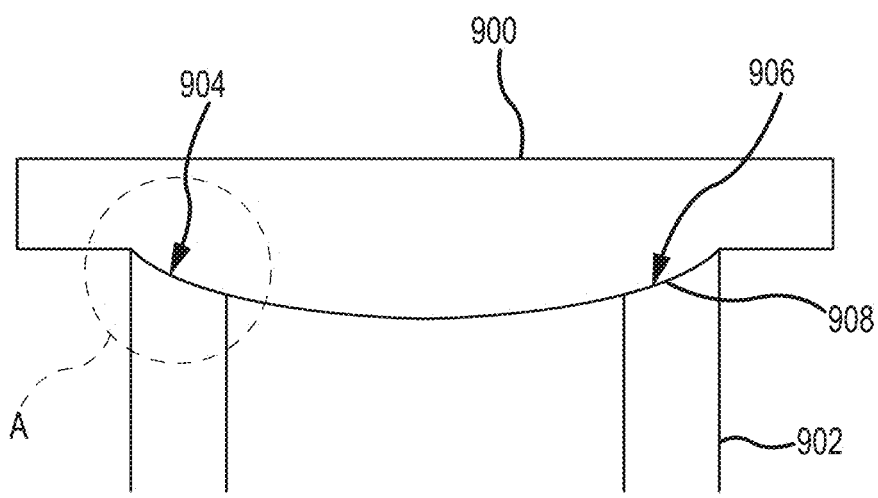

FIG. 9 shows a diaphragm coupled with a coplanar exhalation seat valve according to some embodiments of the invention.

Figure 9A:
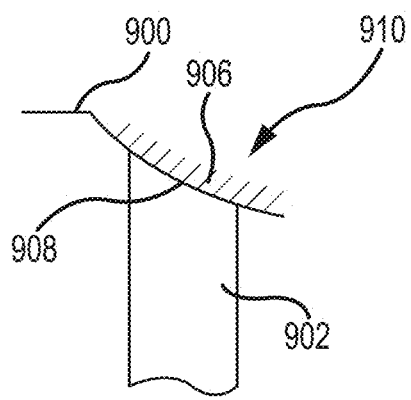
Figure 9B:
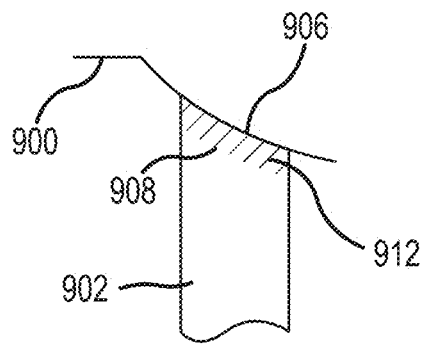

FIGS. 9A and 9B are more detailed views of the seat valve of FIG. 9.

FIGS. 10A, 10B, 10C, and 10D are images of untextured and textured diaphragm surfaces according to some embodiments of the invention.

FIGS. 11A, 11B, 11C, and 11D illustrate methods of using an impedance threshold valve, according to embodiments of the present invention.

FIGS. 12A, 12B, 12C, and 12D illustrate expiration release pressures according to embodiments of the present invention.

DETAILED DESCRIPTION OF THE INVENTION

Embodiments of the present invention encompass systems and methods for enhancing circulation in a patient. These techniques are well suited for use in treating individuals that may suffer from or are at risk of developing a variety of clinical conditions due to low blood flow. For example, exemplary devices and methods can be used to treat subjects presenting sudden cardiac arrest, traumatic injury, heat stroke, fainting, and the like, which can result in or from states of low blood flow or perfusion. In such cases, a lack of adequate blood flow back to the heart can contribute to the low blood pressure. States of low blood flow can impair the body's circulatory function, which delivers oxygen to the body's vital organs and removes toxic cellular waste. Exemplary devices can also be used to stimulate circulation back to the heart and thereby be used as a stress test. They can also be used to modulate the autonomic nervous system, in part by altering baro-receptor sensitivity and function due to an increase in stroke volume and in some cases as a direct effect on airway pressures during each inspiration. Circulatory enhancement techniques disclosed herein can use inspiratory impedance to increase blood flow to the body's vital organs. Further, such approaches can enhance the body's biophysical performance without depending upon pharmaceutical or other outside agents. In many cases, these systems and methods can be used in spontaneously breathing patients or, in cases of non-breathing patients, where body parts are being manipulated to increase venous blood return to the heart, such as, for example, during the performance of CPR. As described herein, inspiration can in some cases refer to both an inhalation phase in a spontaneously breathing patient as well as during the decompression or recoil of the chest of a non-breathing patient being treated with a resuscitation technique, such as CPR, active decompression CPR, using an iron lung device, or the like. As described herein, expiration refers to both an exhalation phase in a spontaneously breathing patient as well as a when the lungs of a non-breathing patient are compressed, such as when the chest is compressed during the performance of CPR.

In devices that completely prevent the flow of respiratory gases, the valves may be configured as pressure responsive valves that open after a threshold negative intrathoracic pressure has been reached, optionally in combination with or as supplemented by an external vacuum. Such systems and devices may be referred to herein collectively by the name impedance threshold device (ITD). ITD's described herein provide a safe, simple, and convenient way to treat states of low blood pressure in spontaneously breathing patients as well as with non-breathing patients. Typically, ITD's include an atmospheric pressure sensing valve or check valve. Such valves can provide therapeutic inspiratory resistance until the patient creates, for example, at least −8 cm $H_2O$ pressure with respiratory effort. Hence, an ITD can provide a therapeutic benefit as soon as a patient begins to breathe through it. These devices have been shown to increase blood pressure during hypotension from a variety of causes, such as orthostatic intolerance, hypovolemia, heat shock, dialysis, blood donation, and the like. During inspiration (or decompression or recoil of the chest), a negative pressure, which is created from expansion of the thorax, draws air into the lungs. When inspiratory impedance is applied to the breathing circuit, it enhances the negative pressure or vacuum in the chest, which pulls more blood back to the heart, resulting in increased preload and thus, enhanced cardiac output on the subsequent cardiac contraction. ITD's can be used on a facemask or with a mouthpiece.

Valve systems according to embodiments of the present invention may incorporate features of ITD's, valves or impeding or preventing mechanisms such as those described in U.S. Pat. Nos. 5,551,420; 5,692,498; 5,730,122; 6,029,667; 6,062,219; 6,155,257; 6,234,916; 6,224,562; 6,526,973; 6,604,523; 6,986,349; and 7,204,251, the complete disclosures of which are herein incorporated by reference. Moreover, it will be appreciated that a wide variety of threshold valve systems can be used. Such devices can be interfaced with a persons' airway to prevent respiratory gas flow to the person's lungs during a portion of an inhalation event to enhance circulation and decreases intracranial pressure, including those described in U.S. Pat. Nos. 6,986,349 and 7,195,012, incorporated herein by reference. Such valve systems enhance circulation by prolonging the duration and increasing the magnitude of negative intrathoracic pressure in the chest to increase venous return. The prevention of gases reentering the thorax during the chest wall recoil phase, or active removal of said gases either intermittently or continuously, results in less and less air in the thorax. Less air in the thorax makes room for more and more blood to return to the heart during the chest wall recoil phase. Additionally, intracranial pressure can be decreased by facilitating the flow of cerebral spinal fluid from the head to the spinal cord and by lowering the intrathoracic pressures during inspiration to repetitively lower pressure in the venous blood vessels out of the head (jugular and vertebral veins) to facilitate venous blood flow out of the head.

In a hypotensive patient, an ITD can improve circulation by providing a slight therapeutic resistance during inspiration, which lowers the intrathoracic pressure and draws more venous blood back to the heart. Improved blood return to the heart (preload) results in improved blood flow out of the heart (cardiac output) during the subsequent cardiac contraction. Thus, despite its placement into the respiratory circuit, an ITD a circulatory enhancer device that provides its therapeutic benefit during the inspiratory phase of respiration.

In a healthy, spontaneously breathing person at rest, the average intrathoracic pressure or upper airway pressure level is about −1.5 cm $H_2O$ during inspiration and about +0.5 cm $H_2O$ during exhalation. When using an ITD, the average intrathoracic pressure or upper airway pressure level can be about −8.0 cm $H_2O$ during inspiration and about +0.5 cm $H_2O$ during exhalation. The greater the negative intrathoracic pressure or vacuum, the more blood that returns to the heart. In addition, the lower intrathoracic pressure causes a decrease in intracranial pressure. In some cases, excessive negative pressures can be detrimental. Embodiments of the present invention provide enhanced negative pressure profiles or waveforms which lead to an increase in blood flow to the heart and brain without excessive changes in negative or positive intrathoracic pressure, among other features.

Changes in intrathoracic pressure are transmitted rapidly to the heart and other organs in the chest. For example, a decrease in pressure within the plural space is transmitted to the right heart, which results in enhanced venous return back to the heart. As the chest wall expands during inspiration, the pressure inside the lungs decreases to sub-atmospheric pressure, thus creating a vacuum relative to the rest of the body. The use of an ITD provides more a negative intrathoracic pressure, resulting in lowered right atrial pressures, which translates to enhanced venous return and greater coronary perfusion pressures. During use, a patient typically feels more resistance during inspiration. Blood pressure and cardiac output increase, and other indicators of perfusion, such as oxygen saturation, pulse strength, skin color, and end tidal carbon dioxide ($ETCO_2$) (an indirect measure of circulation), improve as well. According to some embodiments, supplemental oxygen may be administered to the patient during ITD use.

As used herein, including the appended claims, the term "patient" can mean any person or subject receiving a medical treatment or undergoing a medical procedure, and may include both human and non-human animals.

As used herein including the appended claims, the phrase "airway system" can include any system that is adapted to be interfaced with a patient's airway and has at least one lumen adapted to ventilate the patient's lungs, or is otherwise adapted to move or allow respiratory gases into and out of the patient's airway or lungs. Such airway systems are sometimes referred to herein as "airway adjuncts" or "ventilation tubes". Non-limiting examples of airway systems may include endotracheal tubes, supraglottic airway devices, Combitubes, obturator airways, laryngeal mask airways, and the like. Airway systems as described herein may also include at least a second lumen adapted to deliver oxygen gas into the patient's lungs.

As used herein, the terms "negative pressure" or "vacuum" can refer to a pressure that is less than atmospheric pressure or less than about 760 mm Hg, according to some embodiments. In some cases, the term "negative intrathoracic pressure" refers to a pressure within the thorax, trachea, or intrathoracic cavity of a patient that is below atmospheric pressure; e.g., the intrathoracic pressure values are negative relative to atmospheric pressure. According to embodiments of the present invention, the terms "negative pressure" and "vacuum" may in some cases be used interchangeably.

In some aspects, the features and benefits described herein are achieved by constructing the various components of the valve systems in a certain manner. For example, the surfaces the valve components may be coated or have a certain texture that permit the valve system to function in a way that creates desirable pressure profiles or other features. As described hereinafter, a single valve system may have a valve with a coated surface, one with a textured surface, or both. Further, it will be appreciated that components of the valve systems described below may be interchanged between the various embodiments.

Coated Check Valve Gasket

Turning now to the drawings, FIG. 1A shows aspects of a circulatory enhancement system 100 according to embodiments of the present invention. Circulatory enhancement system 100 includes a valve system 110 that can be coupled with a person's airway. For example, valve system 110 may include a threshold valve 120 and a patient port 130 that interfaces with the patient's airway. As used throughout the description provided herein, the term "patient port" or "ventilation tube" can refer to any patient connection or airway system having a central lumen through which respiratory gases may pass, e.g., an endotracheal tube, laryngeal mask airway device, supraglottic airway device, nasal masks, full face masks, lipseal mouthpieces, and the like. Typically, a patient port or ventilation tube provides a connection or passage to an airway of a patient or individual.

Threshold valve 120 can be configured to prevent or impede respiratory gas flow to the person's lungs during a portion of an inhalation event until the inspiration equals or exceeds an opening pressure of the threshold valve 120. Circulatory enhancement system 100 may also include an external vacuum source 140 that is configured to constantly apply a small level of external vacuum at a juncture 150 between threshold valve 120 and patient port 130. In some embodiments, there is no external vacuum source 140. As shown here, juncture 150 is disposed downstream of threshold valve 120, or otherwise downstream of the interface between check valve gasket 122 and valve seat 124, and upstream of patient port 130. Valve seat 124 surrounds or defines an opening or passage 126 through which air or gas may flow when threshold valve 120 is in an open configuration. In the embodiment depicted here, check valve gasket 122 is disposed against valve seat 124, and thus opening or passage 126 is closed. Vacuum source 140 operates to provide a small level of external vacuum that encourages inspiration. System 100 can be used to increase the respiratory rate and encourage spontaneous respiration of a patient. FIG. 1A illustrates a valve configuration where inspiration has been initiated, but the inspiration does not yet equal or exceed the opening pressure of the threshold valve 120, and hence the threshold valve 120 is closed. Hence, at the outset of the inspiration, the valve system 110 prevents or impedes respiratory gases from flowing into the lungs until a threshold negative intrathoracic pressure level is met or exceeded. Air or gas flow, as depicted by arrow A1, does not travel past the threshold valve 120 and toward the patient or person.

According to some embodiments, the exterior housing 102 includes a polycarbonate material, the interior components, such as valve seat 124 and an exhalation valve seat 164, include a polycarbonate material, a diaphragm 162 includes silicone, the check valve gasket 122 includes silicone, and a resistance member 128 includes a nickel coated material. A patient port 130 may have an inner diameter of about 15 millimeters and an outer diameter of about 22 millimeters. The threshold valve 120 may have a valve cracking pressure in the range from about −2 cm $H_2O$ to about −20 cm $H_2O$, and in some cases of about −8 cm $H_2O$.

The circulatory enhancement system 100 can be used by interfacing valve system 110 to a person's airway. In some cases, valve gasket 122 is provided with a non-stick coating as described in greater detail hereinafter. The non-stick coating can reduce the cracking pressure of the threshold valve 120. Check valve gasket 122 is configured to prevent or impede respiratory gas flow to the person's lungs during a portion of inspiration until the inspiration equals or exceeds an opening pressure of the threshold valve 120. In some embodiments, the threshold valve 120 can be configured to provide a peak intrathoracic pressure of less than about −12 cm $H_2O$ and in some cases less than about −10 cm $H_2O$ during an inspiration phase. In some applications, coated threshold valve 120 may be configured to provide a peak intrathoracic pressure of about −8 cm $H_2O$ and an intrathoracic pressure plateau of less than −10 cm $H_2O$ during inspiration. In some cases, the coated threshold valve provides an intrathoracic pressure plateau of less than −5 cm $H_2O$, and in other cases less than −4 cm $H_2O$ during inspiration. In some cases, threshold valve may be configured to provide a ratio of peak intrathoracic pressure to intrathoracic pressure plateau of about 8:5.

FIG. 1B schematically illustrates the physiological or anatomical status of a patient corresponding to the valve configuration depicted in FIG. 1A. During inhalation as respiratory muscles are activated, the ribcage elevates and expands, and the diaphragm begins to contract downward pushing against the abdomen, as indicated by arrows B1. This requires work, and can be referred to as the active phase of respiration. When the size of the internal thoracic space or volume increases, there is a corresponding reduction in intrathoracic pressure (ITP). Hence, spontaneous inspiration and spontaneous inspiratory efforts can lead to a decrease in intrathoracic pressure. A similar physiological condition is achieved while performing CPR during the decompression or recoil of the person's chest. At this initial stage of a respiratory cycle, the valve 120 is in a closed configuration. Inspiration may have just begun, followed by a decrease in intrathoracic pressure. However, the intrathoracic pressure, optionally in combination with or as supplemented by the external vacuum, is not sufficient to overcome the cracking limit of the valve, and thus the valve remains in the closed configuration and air is not freely flowing into the lungs 190. For example, the external vacuum may provide a pressure of about −4 cm $H_2O$ and the threshold valve may be set to open at an actuating pressure of about −12 cm $H_2O$. In some cases, there may be no external vacuum, and the threshold valve 120 may be set to open at an actuating pressure of about −8 cm $H_2O$.

FIG. 2A shows another configuration of circulatory enhancement system 100 as the inspiration equals or exceeds the opening pressure of the threshold valve 120. When the intrathoracic pressure, optionally in combination with or as supplemented by the external vacuum 140, is sufficient to overcome the cracking limit of the threshold valve 120, then the threshold valve 120 adopts an open configuration. Here, the open configuration of valve system 110 occurs during spontaneous inspiration or when the negative intrathoracic pressure within the chest exceeds the cracking pressure of the threshold valve 120. The sufficiently negative intrathoracic pressure or suction can draw air past the threshold valve 120 and into the lungs due to the resulting vacuum effect. The threshold valve 120 is open and allows airflow to the patient. Hence, when the intrathoracic pressure level, optionally in combination with or as supplemented by the external vacuum, exceeds the cracking pressure of the threshold valve 120, the check valve gasket 122 is pulled or moved downward or away from opening 126 and seat 124, as resistance member 128 is compressed to permit respiratory gases to flow through openings 126 and to the patient's lungs 190. Threshold valve 120 may be set to open when the negative intrathoracic pressure is in the range from about −2 cm $H_2O$ to about −20 cm $H_2O$. In some cases, threshold valve 120 may be set to open when the negative intrathoracic pressure is about −8 cm $H_2O$. The setting of the threshold valve 120 can be determined by the compressibility of resistance member 128, which may include a spring, elastomer, or other resilient or compressible mechanism. Hence, the magnitude and duration of negative intrathoracic pressure may be enhanced during patient inspiration by use of circulatory enhancement system 100. In this way, pressure within the venous blood vessels that transport blood out of the brain is also lowered. In so doing, more blood is drawn out of the brain to reduce intracranial and intraocular pressures. Air or gas flow, as depicted by arrow A2, travels past the threshold valve and toward and into the patient or person.

FIG. 2B schematically illustrates the physiological or anatomical status of a patient corresponding to the valve configuration depicted in FIG. 2A. As inspiration continues, respiratory muscles are more fully activated, the ribcage continues to elevate and expand, and the diaphragm further contracts downward pushing against the abdomen. The growing size of the internal thoracic space or volume leads to further reduction in intrathoracic pressure (ITP). Such a situation also occurs when performing CPR and the chest is actively lifted or permitted to recoil. As the intrathoracic pressure, optionally in combination with or as supplemented by the external vacuum 140, is sufficient to overcome the cracking limit of the valve, the valve 120 adopts an open configuration. For example, the external vacuum in some specific circumstances may provide a pressure of about −4 cm $H_2O$ and the threshold valve may be set to open at an actuating pressure of about −12 cm $H_2O$. In some cases, there may be no external vacuum, and the threshold valve may be set to open at an actuating pressure of about −8 cm $H_2O$.

Figure 3B:
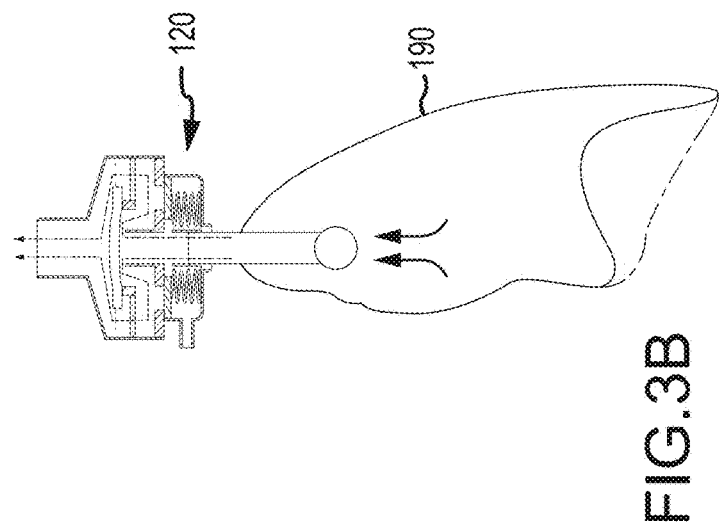
FIGS. 3A and 3B illustrate aspects of a circulatory enhancement system according to embodiments of the present invention.
Figure 3A:
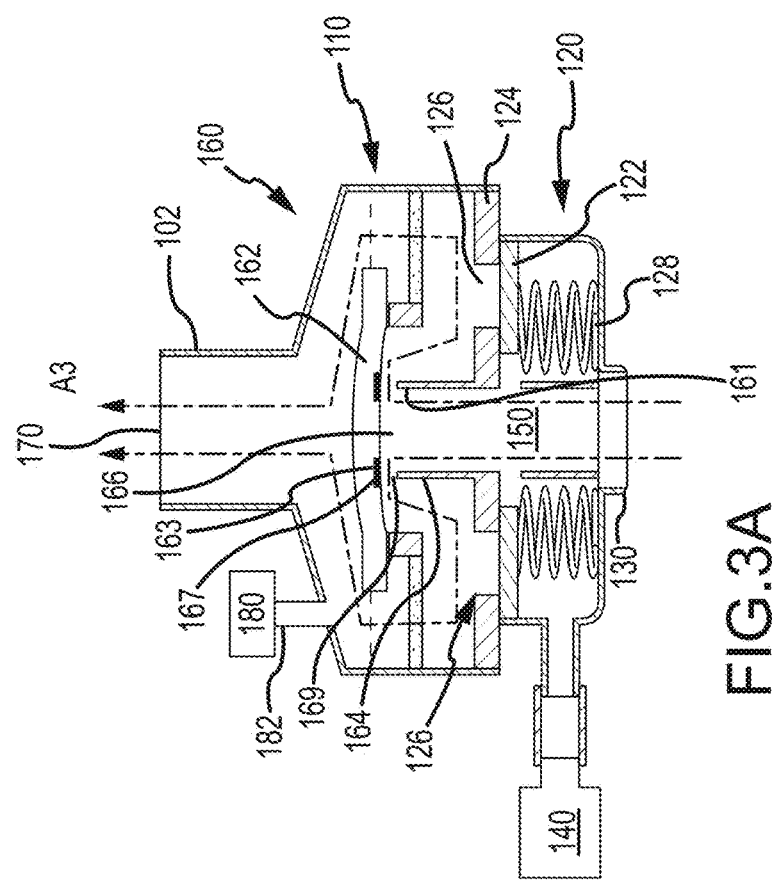

FIG. 3A shows another configuration of circulatory enhancement system 100 as the inspiration becomes less than the opening pressure of the threshold valve 120. When the intrathoracic pressure, optionally in combination with or as supplemented by the external vacuum 140, is no longer sufficient to overcome the cracking limit of the threshold valve 120, then the threshold valve 120 adopts a closed configuration. Once the intrathoracic pressure falls below the threshold, resistance member 128 again closes threshold valve 120 by forcing check valve gasket against openings 126 and valve seat 124, thereby closing the openings 126. Here, the closed configuration of valve system 110 occurs during spontaneous exhalation or when the negative intrathoracic pressure within the chest no longer meets or exceeds the cracking pressure of the threshold valve 120. The threshold valve 120 is closed and does not allow airflow to the patient, whereas an exhalation valve 160 can allow airflow out of the patient. Hence, during the exhalation phase of a breathing cycle, expired gases flow through the system 100, pressing against a diaphragm 162 of an exhalation valve 160, so as to move diaphragm 162 away from an opening 166 and an exhalation valve seat 164, creating an open exhaust channel 167, and thereby opening exhalation valve 160. The gases flow through exhalation valve 160 and exit system 110 through opening 166 or the exhalation port 134. The exhalation valve 160 provides little or no expiratory resistance when opened. Air or gas flow, as depicted by arrow A3, travels past the threshold valve 120 and away from or out of the patient or person.

FIG. 3B schematically illustrates the physiological or anatomical status of a patient corresponding to the valve configuration depicted in FIG. 3A. As inspiration ceases and expiration begins, respiratory muscles relax, the ribcage descends and contracts, and the diaphragm relaxes upward away from the abdomen. The decreasing size of the internal thoracic space or volume leads to an increase in intrathoracic pressure. As the intrathoracic pressure, in combination with or as supplemented by the external vacuum 140, is no longer sufficient to overcome the cracking limit of the threshold valve 120, the threshold valve 120 adopts a closed configuration. Here, airflow is directed from the patient port 130 toward diaphragm 162. Diaphragm 162 is pushed upward and air moves out through an exhalation port 134. In some cases, the external vacuum 140 may provide a pressure of about −4 cm $H_2O$ and the threshold valve 120 may be set to open at an actuating pressure of about −12 cm $H_2O$. In some cases, there may be no external vacuum, and the threshold valve 120 may be set to open at an actuating pressure of about −8 cm $H_2O$.

As indicated in FIGS. 1A and 1B, circulatory enhancement system 100 may include supplemental oxygen port 182 coupled with an oxygen source 180. The oxygen source 180 and oxygen port 182 can be used to supply supplementary oxygen to the patient's lungs. An external vacuum source 140 can be placed at or in fluid communication with a juncture between the valve system 110 and the patient's airway, for example downstream of the threshold valve 120. In some cases, external vacuum source 140 can be placed in fluid communication with any part of the circulatory enhancement system 100 or the patient airway that is downstream of threshold valve 120. In some embodiments, a vacuum or negative pressure is applied downstream of the valve system 110 or threshold valve 120 via a lumen that is separate from the patient port 130. For example, in addition to interfacing patient port 130 with the patient's airway, it is also possible to interface a separate lumen with the patient's airway for the application of vacuum at a location downstream of the threshold valve 120. The vacuum source 140 can provide a small level of external vacuum that encourages inspiration, thereby increasing the respiratory rate and the duration and magnitude of negative intrathoracic pressures generated during each inspiration. In this way, the vacuum 140 can serve to enhance circulation and decrease intracranial pressures to a greater extent than without the external vacuum 140. The duration and magnitude of negative intrathoracic pressure can be increased in several ways. For example, because the patient may be breathing faster, for a given amount of time, the patient may experience more negative intrathoracic pressure than if breathing slower. Second, a continual vacuum can reduce or virtually eliminate the period during inspiration where nothing is happening in the airway (for example, where ITP=0). As such, the effective negative ITP can be much greater for each breathing cycle.

FIG. 4 shows another embodiment of a circulatory enhancement system 470 that in some aspects is similar to circulatory enhancement system 100 and, as described below, circulatory enhancement system 400. As depicted, circulatory enhancement system 470 can include a ventilation cap 472, a diaphragm 474, a check valve cap 476, a check valve gasket 478, a check valve ring 484, a check valve spring 486, and a check valve housing 488. Circulatory enhancement system 470 operates in a manner similar to circulatory enhancement systems 100 and 400 described herein. More specifically, circulatory enhancement system 470 includes a threshold valve formed by the interaction of check valve cap 476 and check valve gasket 478. The threshold valve can be configured to prevent or impede respiratory gas flow to the person's lungs during a portion of inspiration until the inspiration equals or exceeds an opening pressure of the threshold valve. The coating reduces the cracking pressure of a threshold valve formed by the interaction of check valve cap 476 and check valve gasket 478.

As noted above, an ITD may include a check valve gasket or diaphragm having a non-stick coating, such as parylene. FIG. 4A shows aspects of a circulatory enhancement system 400a according to embodiments of the present invention, which includes such a coating. Circulatory enhancement system 400a includes a valve system 410a that can be coupled with a person's airway. For example, valve system 410a may include a threshold valve 420a and a patient port 430a that interfaces with the patient's airway. Optionally, patient port 430a may serve as a patient inspiration port, and may connect with a mouthpiece or facemask. Threshold valve 420a can be configured to prevent or impede respiratory gas flow to the person's lungs during a portion of inspiration until the inspiration equals or exceeds an opening pressure of the threshold valve 420a. Valve seat 424a, which may include a polycarbonate material, surrounds or defines an opening or passage 426a through which air or gas may flow when threshold valve 420a is in an open configuration. Check valve gasket 422a can be disposed against valve seat 424a, and thereby close the opening or passage 426a. When check valve gasket 422a separates away from valve seat 424a as shown here, passage 426a becomes open, and air is allowed to flow through threshold valve 420a and patient port 430a, and into the patient as indicated by arrow A. Check valve gasket 422a is coupled with or incorporates a coating 423a that can contact a seating area 425a of valve seat 424a. As depicted here, coating 423a covers a distal surface 421a of check valve gasket 422a. Check valve gasket 422a can be coated with parylene type N, C, or D, or any combination thereof. For example, coating 423a may include parylene type N. According to some embodiments, a non-stick or stick-resistant coating 423a can have a thickness T within a range from about 0.50 microns to about 1.00 microns. In some cases, coating 423a is about 0.75 microns thick. Coating 423a may be transparent. Coating 423a can prevent or inhibit stickiness or adhesion between valve gasket 422a and valve seat 424a. Coating 423a may also include other non-stick materials, such as Teflon or rubber. In some cases, a check valve gasket can have a roughened surface which provides a non-stick surface. For example, a check valve gasket containing a silicone material, which may otherwise provide excessive stickiness or adhesion between the check valve gasket and the valve seat, can be roughed up so as to make it less sticky. In some cases, a check valve gasket itself contains a material that inhibits or resists adhesion. For example, a check valve gasket can be constructed of a rubber material, which makes the check valve gasket less sticky when compared to a silicone material. In some embodiments, a check valve gasket that is manufactured from a stick-resistant material may have no coating and yet provide the desired wave form or operating characteristics.

FIG. 4B shows aspects of a circulatory enhancement system 400b according to embodiments of the present invention, which includes a coated check valve gasket 422b. Circulatory enhancement system 400b includes a valve system 410b that can be coupled with a person's airway. For example, valve system 410b may include a threshold valve 420b and a patient port 430b that interfaces with the patient's airway. Optionally, patient port 430b may serve as a patient inspiration port, and may connect with a mouthpiece or facemask. Threshold valve 420b can be configured to prevent or impede respiratory gas flow to the person's lungs during a portion of an inspiration until the inspiration equals or exceeds an opening pressure of the threshold valve 420b. Valve seat 424b, which may include a polycarbonate material, surrounds or defines an opening or passage 426b through which air or gas may flow when threshold valve 420b is in an open configuration. Check valve gasket 422b can be disposed against valve seat 424b, and thereby close the opening or passage 426b. When check valve gasket 422b separates away from valve seat 424b as shown here, passage 426b becomes open, and air is allowed to flow through threshold valve 420b and patient port 430b, and into the patient as indicated by arrow B. Check valve gasket 422b is coupled with or incorporates a coating 423b that can contact a seating area 425b of valve seat 424b. As depicted here, coating 423b is disposed on a distal surface 421b of check valve gasket 422b. The coating 423b may include one or more coating elements, such that one coating element 423b' (e.g. an outer coating element) contacts one seating area 425b' (e.g. an outer seating area), and another coating element 423b" (e.g. an inner coating element) contacts another seating area 425b" (e.g. an inner seating area). Check valve gasket 422b can be coated with parylene type N, C, or D, or any combination thereof. For example, coating 423b may include parylene type N. According to some embodiments, a non-stick or stick-resistant coating 423b can have a thickness T within a range from about 0.50 microns to about 1.00 microns. In some cases, coating 423b is about 0.75 microns thick. Coating 423b may be transparent. Coating 423b can prevent or inhibit stickiness or adhesion between valve gasket 422b and valve seat 424b.

FIG. 4C shows aspects of a circulatory enhancement system 400c according to embodiments of the present invention, which includes a coated gasket. Circulatory enhancement system 400c includes a valve system 410c that can be coupled with a person's airway. For example, valve system 410c may include a threshold valve 420c and a patient port 430c that interfaces with the patient's airway. Optionally, patient port 430c may serve as a patient inspiration port, and may connect with a mouthpiece or facemask. Threshold valve 420c can be configured to prevent or impede respiratory gas flow to the person's lungs during a portion of inspiration until the inspiration equals or exceeds an opening pressure of the threshold valve. Valve seat 424c, which may include a polycarbonate material, surrounds or defines an opening or passage 426c through which air or gas may flow when threshold valve 420c is in an open configuration. Check valve gasket 422c can be disposed against valve seat 424c, and thereby close the opening or passage 426c. When check valve gasket 422c separates away from valve seat 424c as shown here, passage 426c becomes open, and air is allowed to flow through threshold valve 420c and patient port 430c, and into the patient as indicated by arrow C. Check valve gasket 422c is coupled with or incorporates a coating 423c that can contact a seating area 425c of valve seat 424c. As depicted here, coating 423c covers all sides of check valve gasket 422c. Check valve gasket 422c can be coated with parylene type N, C, or D, or any combination thereof. For example, coating 423c may include parylene type N. According to some embodiments, non-stick coating 423c can have a thickness T within a range from about 0.50 microns to about 1.00 microns. In some cases, coating 423c is about 0.75 microns thick. Coating 423c may be transparent. Coating 423c can prevent or inhibit stickiness or adhesion between valve gasket 422c and valve seat 424c. In some embodiments, a silicone diaphragm can be coated with a material such as parylene to make it less susceptible to saliva.

It has been discovered that coatings such as parylene can provide improved functioning to a threshold valve, for example when applied to a check valve gasket. Similar beneficial properties can be achieved with check valve gaskets constructed of other non-stick materials. FIG. 5A shows a pressure waveform 500 obtained from an ITD having a non-coated check valve gasket. As depicted here, the inspiration waveform 502 is triangular in shape. During the inspiration phase there is a dramatic drop in ITP to a peak pressure 504 of about −11 cm $H_2O$, followed by a quick rebound to a plateau pressure 506 of about −4 $H_2O$ cm. In contrast, FIG. 5B shows a pressure waveform 510 obtained from an ITD having a coated check valve gasket. As depicted here, the inspiration waveform 512 is square in shape. During inspiration there is an initial drop in ITP to a peak pressure 514 of about −8 cm $H_2O$, followed by a gradual increase in ITP to about −5 cm $H_2O$. Hence, the advantages of a coated check valve are well illustrated by these figures. Because the peak negative ITP is less intense in the ITD with the coated gasket, it is easier for the patient to breathe through this ITD. The patient has to generate a less negative ITP (e.g. −8 cm $H_2O$, as compared to −11 cm $H_2O$) in order to overcome the cracking limit of the check valve. Moreover, the ITD with the coated gasket provides a greater net vacuum. In other words, during the time that the inhalation is in the negative portion of the pressure curve, there is a greater cumulative negative pressure for the coated gasket, as compared with the non-coated gasket.

As depicted in FIG. 5B, for the ITD with the coated gasket, the ITP remains at less than about −5 cm $H_2O$ throughout almost all of the inspiration phase. In contrast, for the ITD with the non-coated gasket, the ITP is greater than about −5 cm $H_2O$ throughout a significant portion of inspiration. These beneficial factors associated with the coated valve gasket lead to enhanced circulation in the patient.

The time units shown in FIGS. 5A and 5B are in seconds. Although it can vary from person to person, and according to the person's individual breathing parameters, inspiration is typically about 2 seconds, and expiration is typically about 1.5 seconds. The ITD may encourage a patient to breathe more deeply, lengthening the inspiration time. According to some embodiments, peak inspiratory pressures with an ITD can range from about −5 cm $H_2O$ to about −15 cm $H_2O$. According to some embodiments, plateau inspiratory pressures with an ITD can range from about −3 cm $H_2O$ to about −13 cm $H_2O$. According to some embodiments, a peak:plateau ratio pressure with an ITD can range from about (−5 to −15):(−3 to −13). A square wave form such as that shown in FIG. 5B can maximize the area under the waveform curve, which thereby should improve preload and circulation. According to some embodiments, peak inspiratory pressures with an ITD having a coated check valve gasket can range from about −4 cm $H_2O$ to about −9 cm $H_2O$. According to some embodiments, peak inspiratory pressures with an ITD can be about −8 cm $H_2O$. A square like wave form can also make it easier for a person to breathe through the ITD device, as the person does not have to overcome the initial effort to open up the valve as shown in the triangular waveform of FIG. 5A.

Without being bound by any particular theory, it is thought that valve gasket function may be less than optimal under certain conditions. For example, valve gasket function may exhibit sub optimal performance in operational conditions such as excessive temperature and humidity. Relatedly, valve gaskets may become warm or moist during use with a breathing patient. Conditions like these may lead to unwanted stickiness or adhesion between the valve gasket and the valve seat or check valve housing. In some cases, valve gaskets made of silicone may be particularly prone to stickiness or adhesion under certain conditions, including warm temperature and high humidity or wetness. Coated gaskets may eliminate or reduce such stickiness or adhesion between the gasket and the seating area of the valve seat. Hence, coated gaskets may be desirable for use with breathing patients even under a wide range of extreme temperatures and humidity conditions.

Textured Diaphragm Valve

Referring back to FIG. 1A an exhalation valve 160 is shown within system 100. System 100 can also include a flexible diaphragm 162 that can act to seal or open an opening 166 of exhalation valve 160 defined by an exhalation valve seat 164. Diaphragm 162 can flex or move up or down based on the flow of gas within system 100. Here, diaphragm 162 is flexed toward the exhalation valve seat 164, and is sealed against a distal surface 161 of exhalation valve seat 164. In some embodiments, diaphragm 162 and/or exhalation valve seat 164 may have a textured surface 167. As depicted here, the textured surface 167 can cover at least a portion of an sealing surface 163 of diaphragm 162. By incorporating the textured surface 167, the reduction of hysteresis can be achieved without increasing valve leakage rates. Further operation details of the textured surface 167 are described below. Although not shown here, the textured surface may be formed on distal surface 161 of exhalation valve seat 164 instead of on the interaction surface 163 of diaphragm 162. The textured distal surface 161 of exhalation valve seat 164 can be positioned to be in contact with the interaction surface 163 of diaphragm 162 when in a closed configuration. One or both of distal surface 161 and sealing surface 163 may be textured.

In some embodiments, the exhalation valve seat 164 can be in the form of a conduit having distal surface 161 that is substantially planar in geometry. The diaphragm 162 is positionable against the distal surface 161 to create an interface between at least a portion of the diaphragm 162 and at least a portion of the distal surface 161, wherein one of the diaphragm 162 and the distal surface 161 comprises a textured surface 167 at the interface. Pressure within the conduit is configured to move the diaphragm 162 away from the distal surface 161 to allow gases to flow through the conduit and around the diaphragm 162 when an expiratory pressure upstream of the diaphragm 162 is greater than about 0.5 cm $H_2O$. The textured surface 167 ensures that leakage of the exhalation valve 160 is below about 0.5 lpm when the diaphragm 162 is interfaced with the distal surface 161. Preferably, the leakage of the exhalation valve 160 is below about 0.05 lpm with the diaphragm 162 is interfaced with the distal surface 161.

Diaphragm 162 is positioned across exhalation valve seat 164 and engages distal surface 161 of the exhalation valve seat 164 and is configured to prevent or impede respiratory gas flow to the person's lungs until the expiration equals or exceeds an opening pressure of the exhalation valve. The impedance of respiratory gas flow can be during a portion of an exhalation event. When the expiration equals or exceeds an opening pressure of the exhalation valve the diaphragm 162 disengages from the distal surface 161 to create an open exhaust channel 169, as shown in FIG. 3A. Exhalation valve 160 is configured to provide a substantially constant expiratory intrathoracic pressure of about 0 cm $H_2O$ during exhalation. Although the exhalation valve 160 includes a textured surface 167 to form a seal interface, the exhalation valve 160 prevents leakage through the seal interface during inspiration. In other words, all incoming respiratory gas flows in through the threshold valve 120. The textured surface 167 ensures that leakage of the exhalation valve 160 is below about 0.5 lpm when the diaphragm 162 is interfaced with the distal surface 161. Preferably, the leakage of the exhalation valve 160 is below about 0.05 lpm with the diaphragm 162 is interfaced with the distal surface 161.

In some embodiments, the inclusion of a textured diaphragm or exhalation valve seat may be used in conjunction with a coated check gasket valve. Such a combination can provide desired hysteresis and leakage rates, both during inspiration and expiration phases. In some embodiments, the threshold valve and exhalation valve can be a single bi-directional valve. For example, a fishmouth valve could provide both inspiratory and expiratory functions.

Referring again to FIG. 2A where inspiration equals or exceeds the opening pressure of the threshold valve 120, the diaphragm 162 is flexed downward and abuts exhalation valve seat 164, sealing passage 166. Although the exhalation valve 160 includes a textured surface 167 to form a seal interface, the exhalation valve 160 prevents leakage through the seal interface during inhalation. In other words, all incoming respiratory gas flows in through the threshold valve 120.

FIG. 3A shows another configuration of circulatory enhancement system 100 as the inspiration becomes less than the opening pressure of the threshold valve 120. Here, the closed configuration of valve system 110 occurs during expiration or when the negative intrathoracic pressure within the chest no longer meets or exceeds the cracking pressure of the threshold valve 120. The threshold valve 120 is closed and does not allow airflow to the patient, whereas an exhalation valve 160 can allow airflow out of the patient. Hence, during expiration, expired gases flow through the system 100, pressing against diaphragm 162 of exhalation valve 160, so as to flex and move diaphragm 162 away from opening 166 and exhalation valve seat 164, creating an open exhaust channel 169, and thereby opening the exhalation valve 160. The gases flow past the exhalation valve 160 and exit the system through opening or exhalation port 170. As discussed with regard to FIG. 1A, diaphragm 162 or exhalation valve seat 164 may have a textured surface 167 to provide a desired low level of surface tension and thus, provide a desired low level of opening pressure hysteresis. Air or gas flow, as depicted by arrow A3, travels past the threshold valve 120 and away from or out of the patient or person.

Referring back to FIG. 4A diaphragm 462 can also optionally include a roughened or textured surface 467 that can contact a seating area 463 of exhalation valve seat 464. As depicted here, the textured surface 467 covers at least a portion of a distal surface 461 of diaphragm 462. For example, the surface may include one or more bumps, grooves, or any other non-smooth surface. Diaphragm 462 can be texturized by sandblasting or through the use of tooling. Alternatively, the textured surface 467 can be formed or molded into diaphragm 462. For example, a formal texture such as a MT-11000 to MT-11020 may be formed into the diaphragm 462. Preferably, the formal texture comprises a MT-11000 surface. The texture can be random or a pattern and does not need to cover the entire interaction surface area of the exhalation valve seat 464. The textured surface 467 can be texturized at a depth of between 0.0005 and 0.0025 inches. Preferably, the texture depth is between 0.0005 and 0.001 inches. This texture can significantly provide a desired low level of valve hysteresis and/or valve hysteresis can be tailored for specific applications. For example, hysteresis pressure that is required by an operating fluid to open the valve is reduced from 5 cm $H_2O$ to less than 0.5 cm $H_2O$. By incorporating the textured surface 467, the reduction of hysteresis can be achieved without increasing valve leakage rates. In some embodiments, the diaphragm may be smooth and the exhalation valve seat may be textured.

In some embodiments, the inclusion of a textured diaphragm or exhalation valve seat may be used in conjunction with a coated check gasket valve. Such a combination can provide desired hysteresis and leakage rates, both during inspiration and expiration phases. The exhalation valve 460 and related components of FIGS. 4B and 4C can have similar properties as described above. Diaphragm 474 of FIG. 4 can have also a textured surface to provide a desired low level of hysteresis.

Referring back to FIG. 5A, an expiration waveform 508 is triangular and peaks between about 2 cm $H_2O$ and 3 cm $H_2O$. In contrast, FIG. 5B shows an expiration pressure waveform 518 obtained from an ITD having a textured diaphragm. Noticeably different is the expiration pressure waveform 518. The ITD having a textured diaphragm has a substantially constant pressure 518 of approximately 0 cm $H_2O$ and is square in shape. The consistent pressure ensures precise actuation of the exhalation valve relative to atmospheric pressure. This precision contributes to the operation of a predictable and reliable system. Some embodiments utilize a textured diaphragm in conjunction with a coated check gasket valve.

According to some embodiments that do not utilize a textured diaphragm, the expiratory pressure, pressure in the lungs above atmospheric pressure that exists at the end of expiration, with an ITD is between about 0 cm $H_2O$ and 3 cm $H_2O$. In embodiments which include a textured diaphragm, the expiratory pressure of an ITD can be substantially constant around 0 cm $H_2O$. Such a low, relatively constant expiratory pressure relates to a lower surface tension and results in a lower opening pressure release of the diaphragm. Additionally, the more consistent release pressures ensure a more predictable and reliable functioning of the valve system.

FIGS. 6A and 6B depict box plots of hysteresis on release pressure to open a valve within a valve system. As it relates to the present invention, hysteresis is a phenomenon that creates different valve opening and closing pressures at the same valve opening. Hysteresis is often caused by the sticking between the valve seat and the sealing mechanism, such as a diaphragm. By reducing the sticking, the opening pressures and closing pressures can be reduced and can become more precise, leading to more predictable actuation of a valve system. In FIG. 6A, the hysteresis level of valve systems utilizing untextured diaphragm surfaces is shown. The valve opening pressure ranges from about 0 cm $H_2O$ to about 4 cm $H_2O$ for such systems. These untextured diaphragm systems have an interquartile range of about 0 cm $H_2O$ to 3 cm $H_2O$. The median value opening pressure is more than 1 cm $H_2O$. In FIG. 6B, a valve system utilizing a textured diaphragm has a valve opening pressure of approximately 0.5 cm $H_2O$. The textured diaphragm effectively reduces hysteresis within the valve system. The median of this data is much closer to 0, approximately 0.15 cm $H_2O$. Both the range and the interquartile range are about 0.5 cm $H_2O$. The much lower median of this data, closer to 0 cm $H_2O$, indicates that the hysteresis is reduced in such systems. Additionally, the tightening of the ranges in the textured device plot indicate a much more consistent set of results, allowing for greater predictability within systems utilizing textured diaphragms.

FIG. 7 illustrates one embodiment of a textured diaphragm 700 of a valve system. The diaphragm 700 may be formed from a single-piece construction. Alternative embodiments can utilize a multiple-piece construction where the selection of materials and shapes allows the diaphragm 700 to retain its flexibility. The diaphragm 700 may be formed from any material that is flexible or that can be made to flex at certain thicknesses. For example, silicon can be used to construct the diaphragm 700. The diaphragm 700 may include one or more textured portions 702. The diaphragm 700 may further include a flexible element 704. The flexible element 704 can be formed by thinning a portion 706 of the diaphragm 700 to allow for a controlled deflection of a sealing surface 708 of the diaphragm 700. The textured portion 702 can be in any shape or pattern. For example, textured portion 702 may be in a concentric pattern with flexible element 704 to provide areas 710 with less adhesion combined with areas of greater adhesion. In this way, the surface finish may be tailored to provide different release patterns based on any desired operating parameters of a valve system. Diaphragm 700 can be texturized by sandblasting or use of tooling. Alternatively, texturized portion 702 can be formed or molded into diaphragm 700. For example, a formal texture such as a MT-11000 to MT-11020 may be formed into the diaphragm 700. Preferably, the formal texture comprises a MT-11000 surface. The texture can be random or a pattern and does not need to cover the entire interaction surface area of the diaphragm 700. The texturized portion 702 can be texturized at a depth of between 0.0005 and 0.0025 inches. This texture can significantly reduce valve hysteresis and/or valve hysteresis can be tailored for specific applications. For example, hysteresis pressure that is required by an operating fluid to open the valve is reduced from 5 cm $H_2O$ to less than 0.5 cm $H_2O$. By incorporating the texturized portion 702, the reduction of hysteresis can be achieved without altering valve leakage rates.

Additionally, the textured diaphragm 700 can act as a valve pressure sensor. Due to the increased consistency and ultimate predictability associated with the textured diaphragm 1200, the open or closed position of the textured diaphragm 700 indicates whether the pressure level within the valve system is less than or greater than relative atmospheric pressure. The low level of hysteresis ensures that the opening pressure remains low, approximately 0 cm $H_2O$, and provides precise valve actuation. By knowing whether the exhalation valve is open or closed, it can be reliably determined whether a patient's thoracic cavity is in a state of vacuum, within 1 cm $H_2O$. When the exhalation valve is open, the ITP is positive relative to atmospheric pressure. When the exhalation valve is closed, the ITP is negative relative to atmospheric pressure. Because the valve system operates based on relative atmospheric pressure, the exhalation valve can be used as a pressure sensor at any location worldwide. The textured valve can further be coupled with an electronic monitoring system to assess and utilize changes in pressure within the airway. This signal can be used, in turn, to record the number of times the person using the device alters the pressure in their airway to levels above or below atmospheric pressure. In some embodiments, using the textured valve and an electronic monitoring system provides a means to measure respiratory rate and inspiratory or expiratory force.

An atmospheric pressure sensor system can prevent all respiratory gas exchange when the pressure inside of a patient's airway is less than atmospheric pressure. Atmospheric sensor systems can include a diaphragm, and the diaphragm can have a textured surface. Atmospheric pressure sensor systems can include a sub-atmospheric pressure valve that opens at a predetermined sub-atmospheric pressure to allow respiratory gases to enter the patient's lungs. Atmospheric pressure sensor systems can also include a resistance regulator that controls expiratory resistance to allow for a range of resistance values between less than 1 cm $H_2O$ at a flow rate of 20 lpm to up to 8 cm of water at a flow rate of 20 lpm. In some cases, such as for a patient being treated with CPR, the resistance regulator can allow for a range of resistance values between less than 1 cm $H_2O$ at a flow rate of 20 lpm to up to 5 cm of water at a flow rate of 20 lpm. Atmospheric sensor systems can detect changes in the patient's airway. These detected changes can be used to give a device user feedback related to the therapy that is delivered.

Valve systems can include other sensors. For example, pressure sensors can be included to monitor the actual pressure within the valve system. Other sensors may be included to monitor a compression or breathing cycle rate of a patient using the valve system. In another embodiment, a sensor can monitor a depth of a chest compression during a compression phase of CPR. It will be understood by those of ordinary skill in the art that other sensor s may be incorporated into valve systems to monitor various aspects of the valve system and/or the patient.

FIG. 8 shows a cross-section of one embodiment of a control valve 800. Control valve 800 includes a diaphragm 802 that is movably positioned relative to an exhalation valve seat 804. Diaphragm 802 can be configured to create a preferential zone 816 for controlled deflection to take place. Although shown here as a u-shape, preferential zone 816 may be achieved using many geometries. When the pressure at a position 806 within control valve 800 is greater than relative atmospheric pressure, there is a gap between diaphragm 802 and exhalation valve seat 804. In this orientation, air is able to flow from a patient through the gap during an expiration phase. When the pressure at position 806 within control valve 800 is less than relative atmospheric pressure, the diaphragm 802 contacts exhalation valve seat 804, creating a seal to prevent airflow to the patient when the pressure within the control valve is less than the relative atmospheric pressure. Diaphragm 802 and/or exhalation valve seat 804 can have a textured surface. The texture can cover the entire surface of the component or can cover all or part of the component at the interface 808 between diaphragm 802 and exhalation valve seat 804. The surface texture can reduce the surface tension at the interface 808, which acts to reduce hysteresis. Using a textured surface, the reduction of hysteresis can be accomplished without effecting the subsequent resealing of the diaphragm doing chest recoil while performing CPR and/or for a spontaneously breathing patient. Thus, the addition of texture does not increase the leakage rate between the diaphragm 802 and the exhalation valve seat 804.

Control valve 800 further includes a check valve gasket 810 that can interface with a valve seat 812 to form a threshold valve 814. In some embodiments, at least a portion of check valve gasket 810 and valve seat 812 can be coated with a non-stick coating. This coating can help to create reliable and consistent cracking pressure characteristics in the threshold valve 814.

Referring to FIG. 9, a diaphragm 900 is shown coupled with an exhalation valve seat 902. It will be appreciated that diaphragms similar to diaphragm 900 may be used with any of the embodiments described herein An interaction area 904 can be formed from the interface between a sealing surface 906 of diaphragm 900 and sealing surface 908 of exhalation valve seat 902. In some embodiments, the sealing surfaces 906 and 908 can be coplanar. Being coplanar ensures that when the sealing surfaces 906 and 908 are in contact, a sufficient seal can be achieved. As shown here, sealing surface 908 of exhalation valve seat 902 can have a beveled shape to interface with a flexed diaphragm 900. In other embodiments, a sealing surface of an exhalation valve seat can interface with a flat diaphragm and the exhalation valve seat's sealing surface can be flat so as to be coplanar to a sealing surface of the flat diaphragm. FIG. 9A depicts an image of interaction area 904 having a textured surface 910 on sealing surface 906 of diaphragm 900. The textured surface 910 can provide a desired low level of hysteresis within an exhalation valve. FIG. 9B depicts an image of interaction area 904 having a textured surface 912 on sealing surface 908 of exhalation valve seat 902. Like textured surface 910, textured surface 912 can provide a desired low level of hysteresis within an exhalation valve.

Figure 10A:
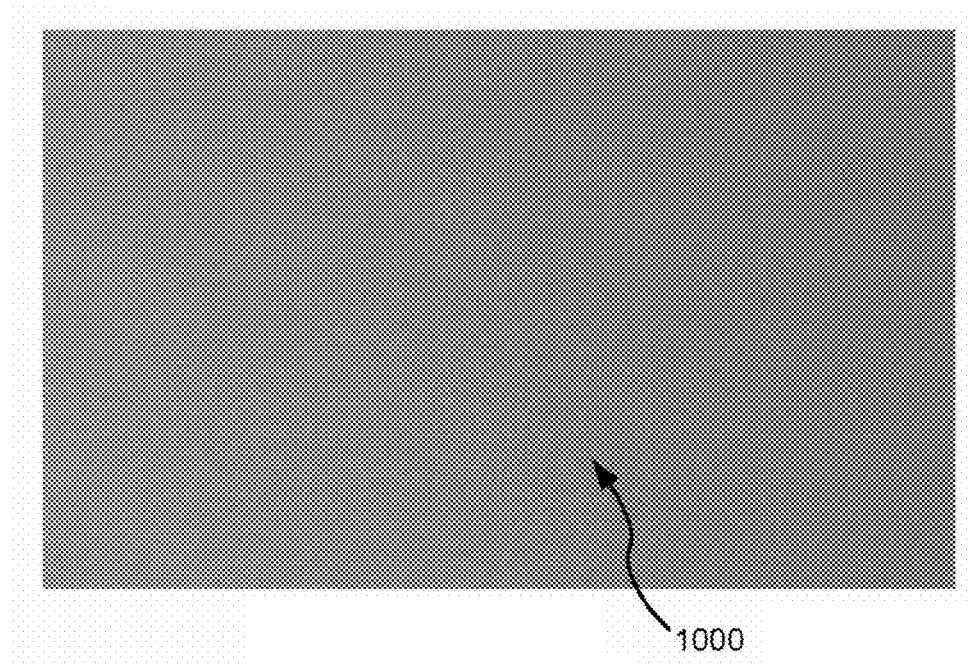
Figure 10B:
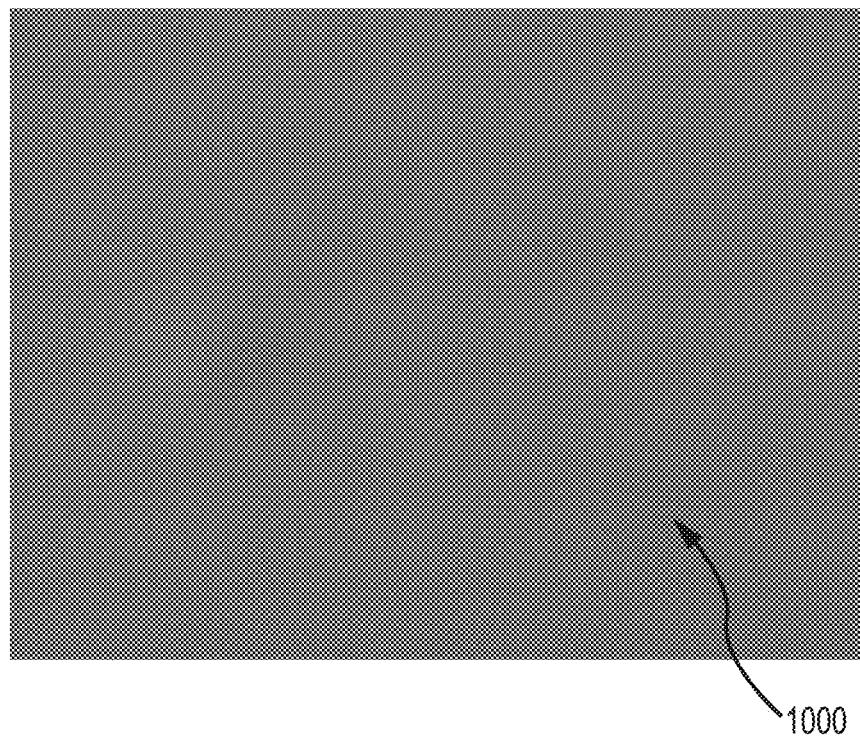
Figure 10C:
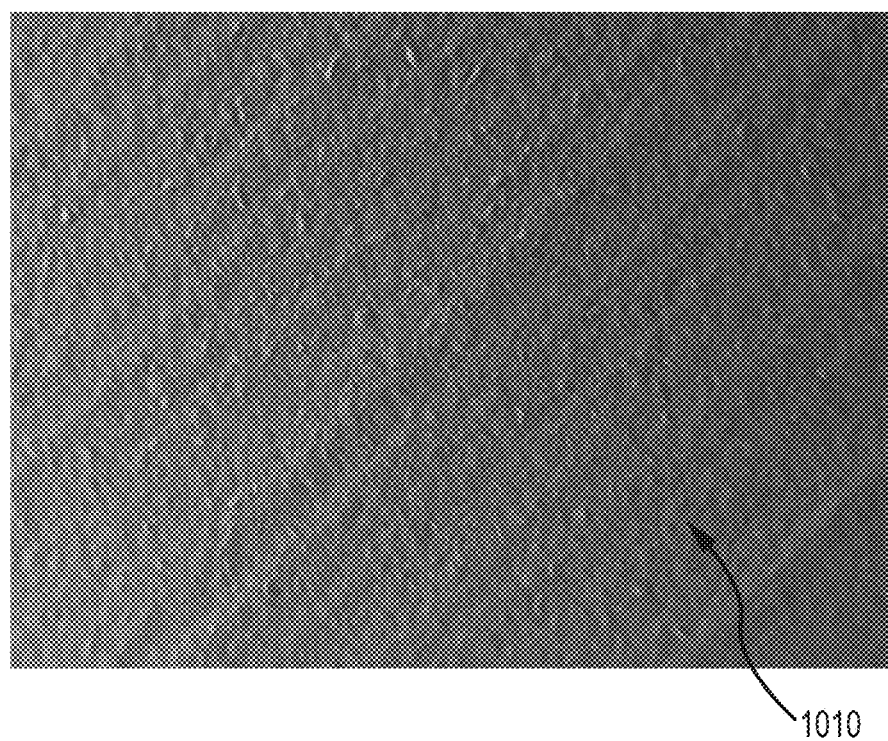
Figure 10D:
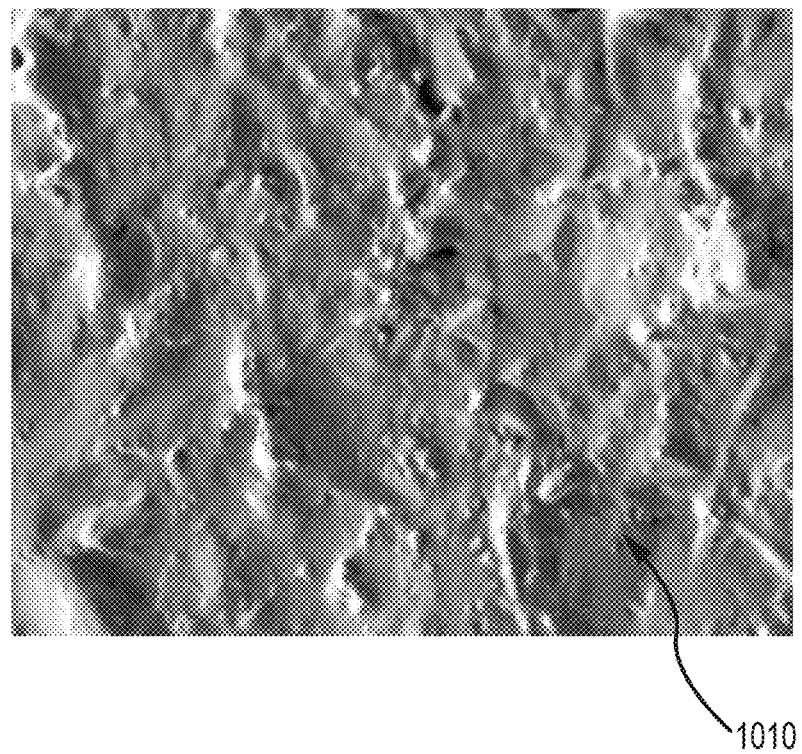

FIGS. 10A to 10D depict surfaces of diaphragms such as those described above. FIG. 10A shows a surface of an untextured diaphragm 1000 at 25× magnification. FIG. 10B shows the same untextured diaphragm surface 1000 at 500× magnification. Even under a relatively high powered magnification, the untextured diaphragm surface 1000 has a very smooth appearance. FIG. 10C shows a textured diaphragm 1010 at 25× magnification. Even at a relatively low magnification, a texture is noticeably visible. Textured diaphragm 1010 is textured at a MT-11000 to MT-11020 standard. For example, the textured diaphragm 1010 can be a MT-11000 standard texture. For example, the textured diaphragm 1010 can be texturized at a depth of between 0.0005 and 0.0025 inches. Preferably, the texture depth is between 0.0005 and 0.001 inches. FIG. 10D shows the same textured diaphragm 1010 at a magnification of 500×. At this magnification, the texture is very apparent, and is in sharp contrast to the untextured diaphragm 1000. These figures illustrate the low level of texture necessary to cause a reduction in hysteresis within a valve system. The texture covers at least a portion of a distal surface of textured diaphragm 1010. As shown here, the textured diaphragm 1010 can include a bumpy surface. In other embodiments, textured diaphragm 1010 can include grooves or any other non-smooth surface. The textured surface of textured diaphragm 1010 can be created by sandblasting or through the use of tooling. Alternatively, the textured surface can be formed or molded into textured diaphragm 1010. This texture can be tailored for specific applications and can provide a desired low level of valve hysteresis. For example, hysteresis pressure that is required by an operating fluid to open the valve can be reduced from 5 cm $H_2O$ to less than 0.5 cm $H_2O$. In some embodiments, the diaphragm may be smooth and an exhalation valve seat may be textured.

The ITD's disclosed herein can be used with any standard facemask, as well as facemasks available from Advanced Circulatory Systems, Inc. which in some cases include expiratory ports that serve to reduce positive-end expiratory pressure (PEEP) (which can decrease preload), reduce the work of breathing, and decrease the opportunity for carbon dioxide retention. A head strap, also available from Advanced Circulatory Systems, Inc., may help obtain and maintain a tight face seal.

Figure 11A:
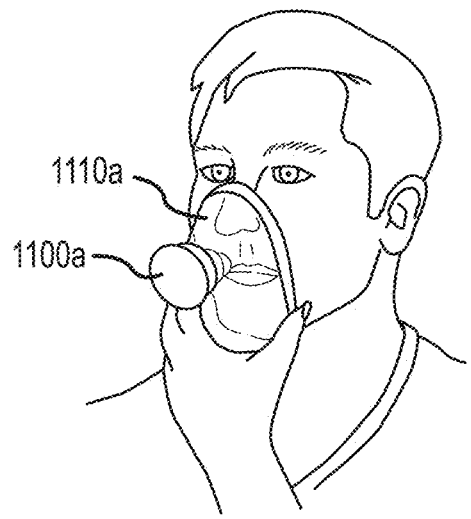
Figure 11B:
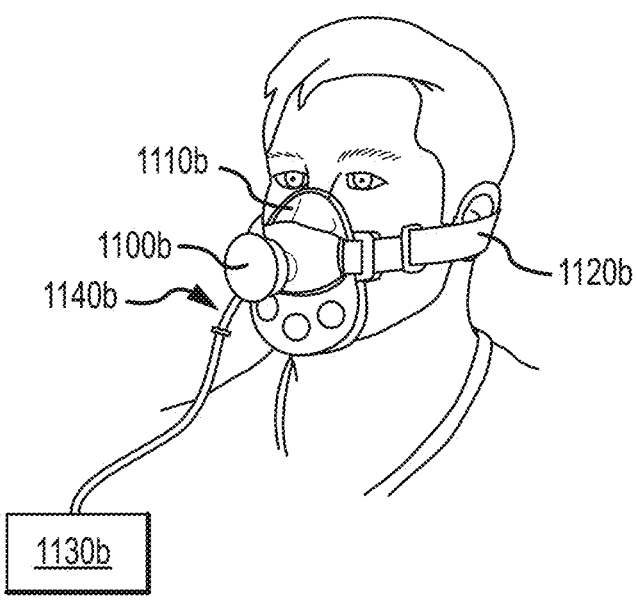
Figure 11C:
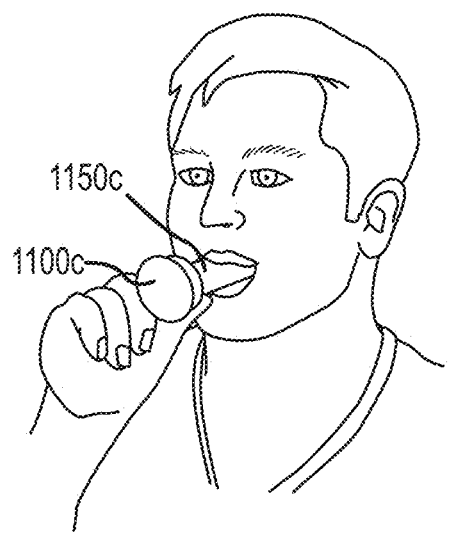
Figure 11D:
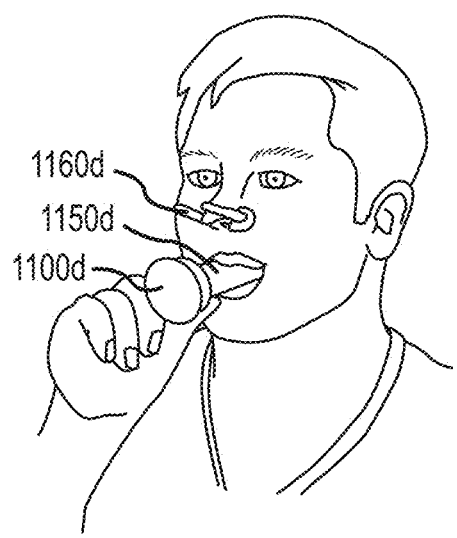

For example, an ITD 1100a can be connected to a facemask 1110a, and the mask can be held over the nose and mouth maintaining a tight facemask seal, as depicted in FIG. 11A. In some cases, a strap 1120b can be used to hold the ITD 1100b and mask 1110b in place, as depicted in FIG. 11B. Optionally, supplemental oxygen can be administered by connecting an oxygen source 1130b to an oxygen port 1140b on the ITD. For example, supplemental oxygen can be supplied to the patient at a rate of about 15 lpm. In some cases, an ITD can be used with a mouthpiece. For example, as shown in FIG. 11C, an ITD 1100c can be connected to a mouthpiece 1150c, and the mouthpiece can be placed in the mouth of the patient maintaining a tight seal with the lips. Optionally, a nose clip 1160d can be applied to the patient, as depicted in FIG. 11D, to prevent or inhibit breathing through the nose, while the patient breathes through the ITD 1100d and mouthpiece 1150d.

Embodiments encompass the use of a valve system that can be coupled with the patient's airway to regulate respiratory gas flows into the lungs. Such a valve system may include a threshold valve that prevents respiratory gases from flowing to the lungs until a certain amount of negative intrathoracic pressure (ITP), optionally in combination with or as supplemented by an external vacuum, is reached. At this point, the valve opens to permit gases to flow to the lungs. Typically, the valve system includes a textured diaphragm. Other embodiments may incorporate a coated check valve gasket in conjunction with the textured diaphragm.

The textured diaphragms and valve coatings as described herein may be incorporated into a wide variety of impeding or preventing mechanisms that prevent or impede respiratory gases from flowing back into the lungs. Valve systems that may utilize the textured diaphragms and valve coatings according to embodiments of the present invention may include those described in U.S. Pat. Nos. 5,551,420; 5,692,498; 5,730,122; 6,029,667; 6,062,219; 6,155,257; 6,234,916; 6,224,562; 6,526,973; 6,604,523; 6,986,349; and 7,204,251, the complete disclosures of which are herein incorporated by reference. Moreover, it will be appreciated that a wide variety of threshold valve systems can be used that incorporate the features described herein. Such valve systems can be interfaced with a persons' airway to prevent respiratory gas flow to the person's lungs during a portion of inspiration to enhance circulation and decreases intracranial pressure, including those described in U.S. Pat. Nos. 6,986,349 and 7,195,012, incorporated herein by reference. Such valve systems enhance circulation by prolonging the duration and increasing the magnitude of negative intrathoracic pressure in the chest to increase venous return. By enhancing the amount of venous blood flow into the heart and lungs, cardiopulmonary circulation is increased. The intracranial pressure is decreased by facilitating the flow of cerebral spinal fluid from the head to the spinal cord and by lowering the intrathoracic pressures during inhalation to repetitively lower pressure in the venous blood vessels out of the head (jugular and vertebral veins) to facilitate venous blood flow out of the head. Impeding or preventing mechanisms may be configured to completely prevent or provide resistance to the inflow of respiratory gases into the patient while the patient inspires. In devices that completely prevent the flow of respiratory gases, the valves may be configured as pressure responsive valves that open after a threshold negative intrathoracic pressure has been reached, optionally in combination with or as supplemented by an external vacuum.

Sample Protocols

As noted elsewhere herein, an ITD provides therapeutic resistance to inspiration in spontaneously breathing patients and as well as non-breathing patients being treated to decrease their intrathoracic pressures. During inspiration, a negative pressure (created from expansion of the thorax) draws air into the lungs. When inspiratory impedance is added or applied to the ventilation or breathing circuit, it enhances the negative pressure (vacuum) in the chest, which pulls more blood back to the heart, resulting in increased preload and thus, enhanced cardiac output on the subsequent cardiac contraction. An ITD provides therapeutic benefit as soon as it is placed into the circuit and may be helpful in establishing intravenous access. ITD use is indicated for patients experiencing symptoms of low blood circulation or hypotension (e.g. <100–110 mmHg [adults]; age dependent in children), which can be secondary to a variety of causes such as dialysis, hypovolemia, dehydration, sepsis and orthostatic intolerance. When using an ITD on a facemask, the operator may connect the ITD to a vented facemask, and hold the facemask over the nose and mouth (or have the patient hold the facemask in place), so as to establish and maintain a tight face seal with facemask. In some cases, a head strap may be used, for example if the patient does not want to hold the ITD and facemask in place. While the ITD and facemask is placed on the patient, the operator may instruct the patient to breathe in slowly (e.g. over 2–3 seconds) and deeply, and to exhale normally. An exemplary breathing rate is about 10-16/minute. If supplemental oxygen is used, the operator may attach an oxygen delivery tubing to the oxygen port on the ITD and deliver oxygen at a rate of one (1) to fifteen (15) lpm. When using an ITD with a mouthpiece, the operator may connect the ITD to the mouthpiece, and lace the mouthpiece into the patient's mouth so as to establish and maintain a tight seal with the lips. The operator can instruct the patient to breathe in slowly (e.g. over 2–3 seconds) and deeply through the mouth only, and to exhale normally. An exemplary breathing rate is about 10-16/minute. A nose clip may be applied to the patient's nose if the patient has trouble inspiring only through their mouth. If supplemental oxygen is used, the operator may attach an oxygen delivery tubing to the oxygen port on the ITD and deliver oxygen at a rate of about one (1) to about fifteen (15) lpm.

An ITD can be used, optionally with a facemask or mouthpiece, to provide a temporary increase in blood circulation during emergency care, hospital, clinic or home use. ITD usage may also be beneficial for patients experiencing hypotension during dialysis and severe blood loss. Techniques described herein may be performed while the patient breathes spontaneously or while assisted ventilation is provided. An assisted mechanical support may optionally be coupled to the patient during the treatment. For example, a body cuirass, iron lung device, vest or other device that alters the intrathoracic pressure, e.g., by transforming the vest into a bellows, may be applied to the patient's chest. In this way, the intrathoracic pressure may be increased and decreased during the treatment. Such a treatment is particularly useful with patients in an Intensive Care Unit. Methods and devices disclosed herein are well suited for treating a patient suffering from heart failure. According to one exemplary method, a facial mask is sealed around the patient's mouth and nose, with the mask including a one-way expiration valve and an inspiratory threshold valve. A threshold valve can be biased to open when a threshold pressure within the mask is in the range from about −3 cm $H_2O$ to about −15 cm $H_2O$. With this arrangement, the patient breathes while the mask is sealed to the face, with the respiratory gasses being prevented from entering the patient's lungs during inspiration until the patient produces a pressure within the mask that is within the range from about −3 cm $H_2O$ to about −15 cm $H_2O$. At this point, the inspiratory valve opens to allow respiratory gasses into the lungs.

EXAMPLES

A patient port of a ResQPOD CPR assist device without a textured diaphragm was connected to a test setup of a vacuum. The vacuum pressure was adjusted to 0.5 cm $H_2O$ and the flow through the device was recorded in lpm. The flow measurements were repeated at 0.5 cm $H_2O$ increments from 1 cm $H_2O$ to 10 cm $H_2O$. The patient port of the ResQPOD was then connected to a test setup for positive pressure. The pressure was adjusted to 0.5 cm $H_2O$ above atmospheric pressure and the flow through the device was recorded in lpm. The flow measurements were then repeated at 0.5 cm $H_2O$ increments from 1 cm $H_2O$ to 10 cm $H_2O$. This process was then repeated for a textured diaphragm ResQPOD, a 60 durometer textured diaphragm ResQPOD, and a 50 durometer textured diaphragm ResQPOD. Valve leakage can be measured by attached a proximal end of the valve mechanism to a custom flow and pressure monitoring system. The system uses a centrifugal blower to generate pressure with a pressure transducer in a closed feedback loop to control the pressure and a TSI flow systems Model 4000 (TSI Inc., Shoreview, Minn.) flow meter to monitor flow. A series of pressures may be generated on the proximal port of the valve and the corresponding flow rates through the valve may be measured. Based on the measured flow rates, a leakage rate can be determined. The results of these tests are shown in FIGS. 12A to 12D. In the graphs, the pressures and corresponding derived flows in vacuum pressure (inspiratory flow and effort) are denoted as positive. Similarly, pressures and corresponding derived flows above atmospheric pressure (expiratory flow and effort) are denoted as negative.

Figure 12A:
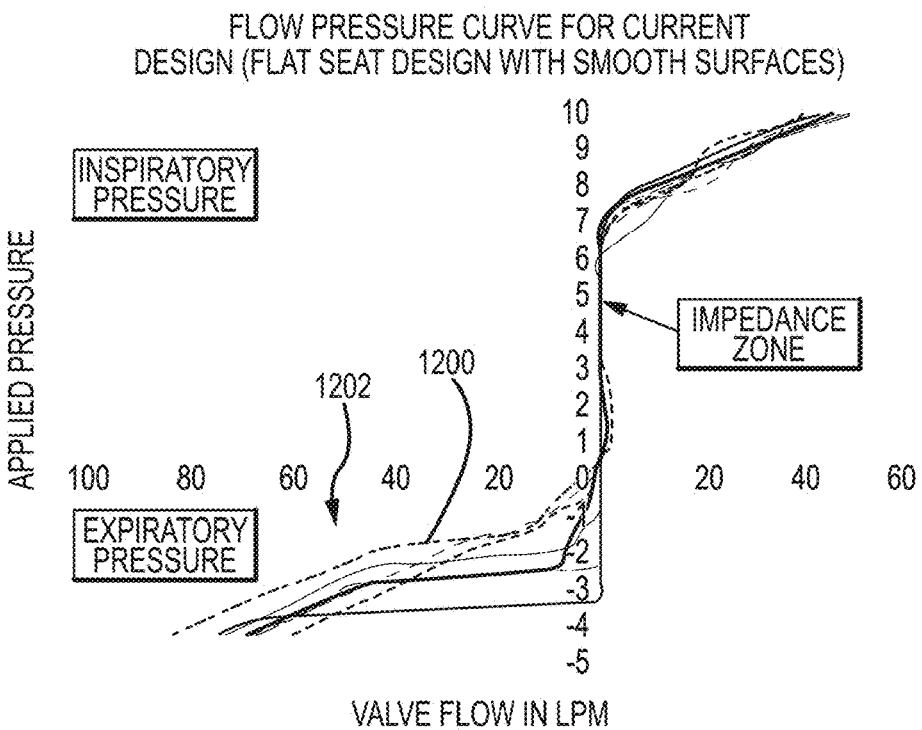
Figure 12B:
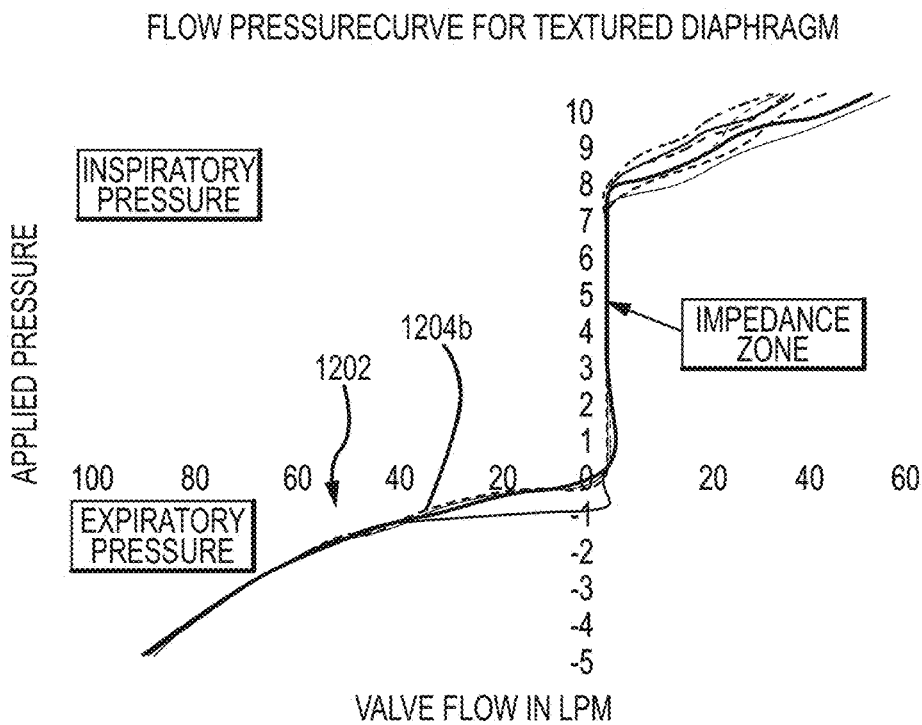
Figure 12C:
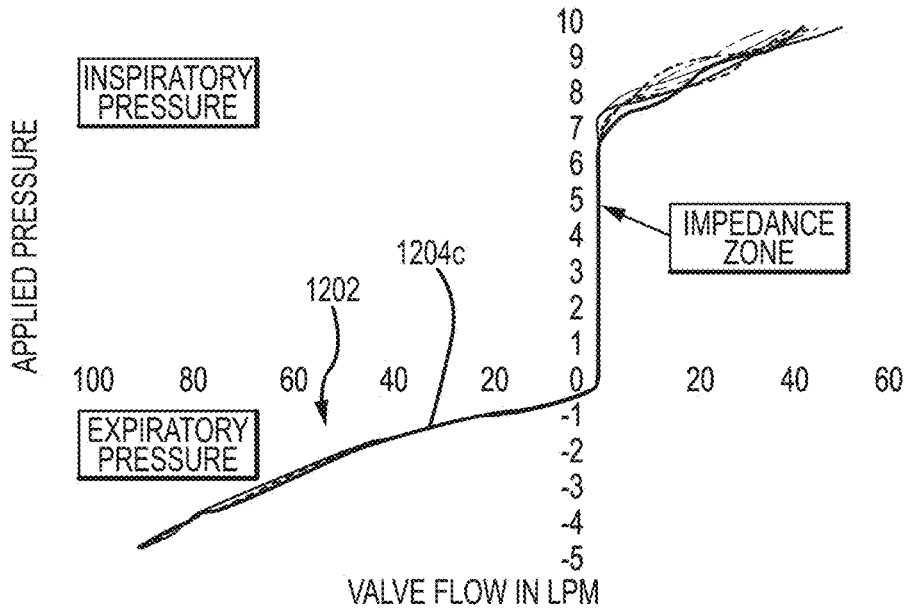
Figure 12D:
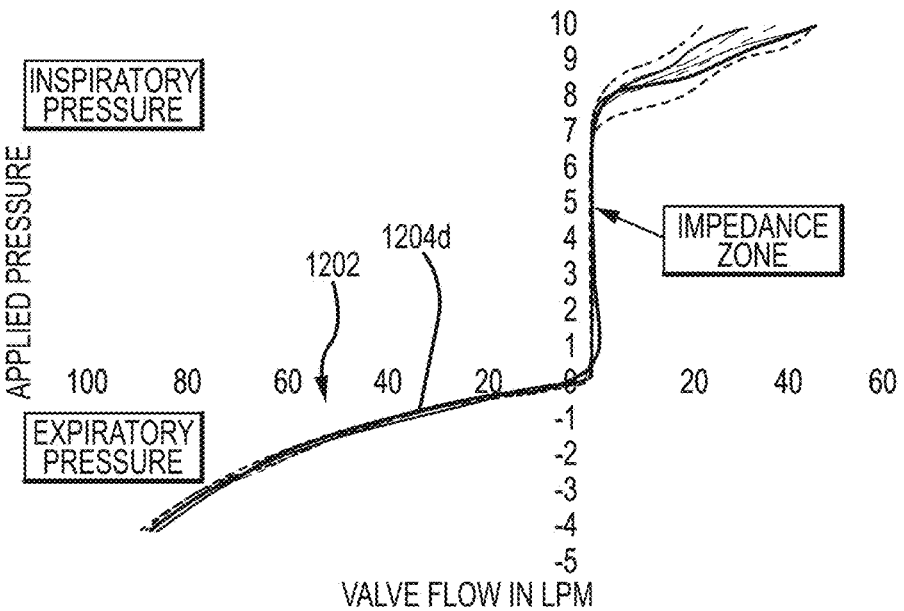

Referring to FIG. 12A, the flow versus pressure characteristic for the ResQPOD device having an untextured diaphragm is shown. The applied expiratory pressure corresponding to the different flow rates varied considerably, as shown by the spread out lines 1200 on the expiratory pressure portion 1202 of the graph. The leakage of the valve system can be seen from the positive valve flow 1206*a*. Looking now at the graphs of FIGS. 12B to 12D, the flow versus pressure characteristic of ResQPOD devices having a textured diaphragm is shown. Here, the applied expiratory pressure is much more consistent. The consistency is shown by the tight grouping of lines 1204*b*, 1204*c*, and 1204*d* on the expiratory pressure portion 1202 of the graph. The consistency and lower pressure release of the diaphragm is a result of lower surface tension attributed to the textured diaphragm. The leakage of the valve system can be seen from the positive valve flows 1206*b*, 1206*c*, and 1206*d*. The more consistent grouping of lines closer to zero on FIGS. 12B to 12D indicate lower leakage rates for the textured diaphragms than the untextured diaphragm of FIG. 12A.

What is claimed is:

1. A system for regulating intrathoracic pressure, the system comprising:
   a valve system that is configured to be coupled with a person's airway, the valve system having an exhalation valve, a threshold valve, and a patient port that interfaces with the person's airway, wherein:
   the exhalation valve comprises a diaphragm and an exhalation valve seat,
   the exhalation valve is configured to retain an intact seal between the diaphragm and a distal end of the exhalation valve seat during inspiration and until an expiratory pressure of the person's airway during expiration equals or exceeds an opening pressure of the exhalation valve, at which time the diaphragm separates from the distal end to create an open exhaust channel between the diaphragm and the distal end, the open exhaust channel permitting expiratory gas flow from the person's airway therethrough,
   the diaphragm is configured to provide a predictable opening pressure while limiting leakage of incoming respiratory gases through the exhalation valve during inspiration or a negative intrathoracic pressure to an acceptable leakage rate of below 0.05 lpm at about −5 cm H$_2$O and when the diaphragm contacts the distal end, and the threshold valve is configured to prevent or impede respiratory gas flow to the person's lungs until an opening pressure of the threshold valve is exceeded, and
   the threshold valve comprising a check valve configured to facilitate opening of the threshold valve at the opening pressure of the threshold valve, and wherein:
   the system comprises a textured surface comprising a plurality of bumps and/or grooves and configured to facilitate opening of the exhalation valve on either a surface of the diaphragm that contacts the distal end of the exhalation valve seat or the distal end of the exhalation valve seat, and/or
   the system comprises a textured surface comprising a plurality of bumps or grooves and configured to facilitate opening of the threshold valve on a surface of the gasket facing a valve seat of the threshold valve or on the valve seat of the threshold valve.

2. The system according to claim 1, wherein the textured surface comprises a standard texture having a value of MT-11000.

3. The system according to claim 1, wherein the opening pressure of the exhalation valve has a value within a range from 0 cm H$_2$O to 8 cm H$_2$O.

4. The system according to claim 1, wherein the opening pressure of the exhalation valve has a value between about 0 cm H$_2$O and 0.5 cm H$_2$O.

5. The system according to claim 1, wherein the opening pressure of the exhalation valve is relative atmospheric pressure or greater.

6. The system according to claim 1, wherein the threshold valve is configured to produce a pressure that is represented by a square pressure waveform during an inspiration phase.

7. The system according to claim 1, wherein the threshold valve is configured to provide a peak intrathoracic pressure of about −8 cm H$_2$O or less during an inspiration phase.

8. The system according to claim 1, wherein the threshold valve is configured to provide an intrathoracic pressure plateau of about −5 cm H$_2$O or less during an inspiration phase.

9. A pressure actuated valve for use in an intrathoracic pressure regulation system, the valve comprising: a conduit having a distal end that is substantially planar in geometry; and a diaphragm that is positionable against the distal end to create an interface between at least a portion of the diaphragm and at least a portion of the distal end, wherein one of the portion of the diaphragm and the portion of the distal end comprises a textured surface comprising a plurality of bumps and/or grooves at the interface, wherein the textured surface is configured to provide a predictable opening pressure while limiting leakage of incoming respiratory gases through the exhalation valve during inspiration or a negative intrathoracic pressure to an acceptable leakage rate of below 0.05 lpm at about −5 cm H$_2$O and when the diaphragm contacts the distal end; wherein the diaphragm is configured to separate from the distal end, thus breaching the interface, to allow gases to flow between the diaphragm and the distal end when an expiratory pressure within the conduit is greater than 0 cm H$_2$O.

10. The pressure actuated valve according to claim 9, wherein the textured surface comprises a texture depth having a value within a range between 0.0005 and 0.001 inches.

11. A method of regulating intrathoracic pressure, the method comprising:
   interfacing a valve system to a person's airway, the valve system having an exhalation valve, a threshold valve, and a patient port that interfaces with the person's airway, wherein:
   the exhalation valve comprises a diaphragm and an exhalation valve seat,
   the exhalation valve is configured to retain an intact seal between the diaphragm and a distal end of the exhalation valve seat during inspiration and until an expiratory pressure of the person's airway during expiration equals or exceeds an opening pressure of the exhalation valve, at which time the diaphragm separates from the distal end to create an open exhaust channel between the diaphragm and the distal end, the open exhaust channel permitting expiratory gas flow from the person's airway therethrough,
   the diaphragm is configured to provide a predictable opening pressure while limiting leakage of incoming respiratory gases through the exhalation valve during inspiration or a negative intrathoracic pressure to an acceptable leakage rate of below 0.05 lpm at −5 cm $H_2O$ and when the diaphragm contacts the distal end, and the threshold valve is configured to prevent or impede respiratory gas flow to the person's lungs until an opening pressure of the threshold valve is exceeded, and the threshold valve comprising a check valve gasket configured to facilitate opening of the threshold valve at the opening pressure of the threshold valve, and wherein:

the system comprises a textured surface comprising a plurality of bumps and/or grooves and configured to facilitate opening of the exhalation valve on either a surface of the diaphragm that contacts the distal end of the exhalation valve seat or the distal end of the exhalation valve seat, and/or the system comprises a textured surface comprising a plurality of bumps and/or grooves and configured to facilitate opening of the threshold valve on a surface of the gasket facing a valve seat of the threshold valve or on the valve seat of the threshold valve.

12. The method of claim 11, wherein the impeded respiratory gas comprises outflowing respiratory gas during a period of expiration.

13. The method according to claim 11, wherein the opening pressure comprises relative atmospheric pressure or greater.

14. The method according to claim 11, wherein the predictable opening pressure comprises a range of pressure values extending between a minimum value and a maximum value such that a difference between the minimum value and the maximum value does not exceed about 0.5 cm $H_2O$.

15. The method according to claim 11, further comprising performing cardiopulmonary resuscitation on the person by repeatedly compressing the person's chest.

16. The method according to claim 15, further comprising actively lifting the person's chest between compressions.

17. The method according claim 11, wherein the person is breathing, and wherein the exhalation valve prevents or impedes respiratory gas flow from the person's airway until the expiratory pressure of the person's airway equals or exceeds the opening pressure of the exhalation valve.

18. The system according to claim 1, wherein the diaphragm comprises a material having a durometer that provides a predictable opening pressure.

* * * * *

UNITED STATES PATENT AND TRADEMARK OFFICE
CERTIFICATE OF CORRECTION

PATENT NO. : 10,265,495 B2
APPLICATION NO. : 14/197996
DATED : April 23, 2019
INVENTOR(S) : Greg Voss et al.

Page 1 of 1

It is certified that error appears in the above-identified patent and that said Letters Patent is hereby corrected as shown below:

In the Claims

Column 32, Line 15, Claim 17, after "according" insert -- to --

Signed and Sealed this
Twenty-fifth Day of June, 2019

Andrei Iancu
*Director of the United States Patent and Trademark Office*